US008669389B2

(12) United States Patent
Cruse et al.

(10) Patent No.: US 8,669,389 B2
(45) Date of Patent: Mar. 11, 2014

(54) BLOCKED MERCAPTOSILANE COUPLING AGENTS, PROCESS FOR MAKING THE USES IN RUBBER

(71) Applicant: Momentive Performance Materials Inc., Albany, NY (US)

(72) Inventors: Richard W. Cruse, Yorktown Heights, NY (US); W. Michael York, Concord, NC (US); Eric R. Pohl, Mt. Kisco, NY (US); Antonio Chaves, Chappaqua, NY (US); Tiberiu L. Simandan, Marletta, OH (US); Prashant Joshi, Gathersburg, MD (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 13/745,070

(22) Filed: Jan. 18, 2013

(65) Prior Publication Data
US 2013/0131250 A1    May 23, 2013

Related U.S. Application Data

(60) Continuation of application No. 12/820,198, filed on Jun. 22, 2010, now Pat. No. 8,383,850, which is a division of application No. 11/647,780, filed on Dec. 28, 2006, now Pat. No. 7,781,606.

(51) Int. Cl.
C07F 7/02    (2006.01)
C07F 7/04    (2006.01)
C07F 7/08    (2006.01)

(52) U.S. Cl.
USPC ........ 556/429; 525/326.1; 524/167; 524/146; 524/168; 524/173; 524/262; 524/265; 524/267

(58) Field of Classification Search
USPC ........ 556/429; 525/326.1; 524/167, 146, 168, 524/173, 262, 265, 267
See application file for complete search history.

(56) References Cited

U.S. PATENT DOCUMENTS

| 3,505,166 A | 4/1970 | Jones et al. |
| 3,624,160 A | 11/1971 | Jones et al. |
| 3,692,812 A | 9/1972 | Berger |
| 3,798,196 A | 3/1974 | Rocklaschal at al. |
| 3,842,111 A | 10/1974 | Meyer-Simon et al. |
| 3,869,340 A | 3/1975 | Kotzsch et al. |
| 3,873,849 A | 3/1975 | Babcock et al. |
| 3,922,436 A | 11/1975 | Bell et al. |
| 3,946,059 A | 3/1976 | Janssen et al. |
| 3,957,718 A | 5/1976 | Pochert et al. |
| 3,978,103 A | 8/1976 | Meyer-Simon et al. |
| 3,997,356 A | 12/1976 | Thum et al. |
| 3,997,581 A | 12/1976 | Pletka et al. |
| 4,044,037 A | 8/1977 | Mui et al. |
| 4,060,539 A | 11/1977 | Seiler et al. |
| 4,072,701 A | 2/1978 | Pletka et al. |
| 4,076,550 A | 2/1978 | Thum et al. |
| 4,099,981 A | 7/1978 | Mui et al. |
| 4,100,172 A | 7/1978 | Mui et al. |
| 4,113,696 A | 9/1978 | Williams et al. |
| 4,125,552 A | 11/1978 | Speier |
| 4,128,438 A | 12/1978 | Wolff et al. |
| 4,129,585 A | 12/1978 | Buder et al. |
| 4,152,347 A | 5/1979 | Pletka |
| 4,184,998 A | 1/1980 | Shippy et al. |
| 4,210,459 A | 7/1980 | Williams et al. |
| 4,222,915 A | 9/1980 | Wolff et al. |
| 4,229,333 A | 10/1980 | Wolff et al. |
| 4,375,988 A | 3/1983 | Mueller et al. |
| 4,384,132 A | 5/1983 | Schwarz et al. |
| 4,408,064 A | 10/1983 | Schwarz et al. |
| 4,444,936 A | 4/1984 | Schwarz et al. |
| 4,507,490 A | 3/1985 | Panster et al. |
| 4,514,231 A | 4/1985 | Kerner et al. |
| 4,517,336 A | 5/1985 | Wolff et al. |
| 4,519,430 A | 5/1985 | Ahmad et al. |
| 4,524,169 A | 6/1985 | Wolff et al. |
| 4,574,133 A | 3/1986 | Umpleby |
| 4,704,414 A | 11/1987 | Kerner et al. |
| 4,709,065 A | 11/1987 | Yoshioka et al. |
| 4,820,751 A | 4/1989 | Takeshita et al. |
| 4,959,153 A | 9/1990 | Bradshaw et al. |
| 4,981,937 A | 1/1991 | Kuriyama et al. |
| 5,037,872 A | 8/1991 | Schwarze et al. |
| 5,110,969 A | 5/1992 | Dittrich et al. |
| 5,116,886 A | 5/1992 | Wolff et al. |
| 5,159,009 A | 10/1992 | Wolff et al. |
| 5,399,739 A | 3/1995 | French et al. |
| 5,401,789 A | 3/1995 | Wolff et al. |
| 5,405,985 A | 4/1995 | Parker et al. |
| 5,466,848 A | 11/1995 | Childress |
| 5,468,893 A | 11/1995 | Parker et al. |
| 5,489,701 A | 2/1996 | Childress et al. |
| 5,596,116 A | 1/1997 | Childress et al. |
| 5,605,951 A | 2/1997 | Sandstrom et al. |
| 5,650,457 A | 7/1997 | Scholl et al. |
| 5,663,226 A | 9/1997 | Scholl et al. |
| 5,663,358 A | 9/1997 | Cohen et al. |
| 5,663,395 A | 9/1997 | Gobel et al. |

(Continued)

FOREIGN PATENT DOCUMENTS

AU    1997/10082    1/1997
CA    991836    6/1976

(Continued)

OTHER PUBLICATIONS

Abstract for Japanese Pat. Appl. Publ. No. 2001-226383. A published Aug. 21, 2001 (Patent Abstracts for Japan. 1 page) (corresp. To FP2 on attached PTO/SB/08a form).

Primary Examiner — James J Seidleck
Assistant Examiner — Deve E Valdez
(74) Attorney, Agent, or Firm — Dominick G. Vicari; Joseph S. Ostroff

(57) ABSTRACT

The invention relates to sulfur silane coupling agents containing multiple blocked mercapto groups which are in a state of reduced activity until activated. The coupling agents are advantageously used in rubber formulations, for example, for fabricating tires with low rolling resistance.

15 Claims, No Drawings

(56) References Cited

U.S. PATENT DOCUMENTS

| | | |
|---|---|---|
| 5,663,396 A | 9/1997 | Musleve et al. |
| 5,672,639 A | 9/1997 | Corvasce et al. |
| 5,674,932 A | 10/1997 | Agostini et al. |
| 5,675,014 A | 10/1997 | Cohen et al. |
| 5,679,728 A | 10/1997 | Kawazura et al. |
| 5,684,172 A | 11/1997 | Wideman |
| 5,698,619 A | 12/1997 | Cohen et al. |
| 5,719,207 A | 2/1998 | Cohen et al. |
| 5,723,529 A | 3/1998 | Bernard et al. |
| 5,728,778 A | 3/1998 | D'Sidocky et al. |
| 5,733,963 A | 3/1998 | Sandstrom et al. |
| 5,753,732 A | 5/1998 | Wideman et al. |
| 5,770,754 A | 6/1998 | Scholl |
| 5,780,531 A | 7/1998 | Scholl |
| 5,817,852 A | 10/1998 | Ichinohe |
| 5,827,912 A | 10/1998 | Scholl |
| 5,859,275 A | 1/1999 | Munzenberg et al. |
| 5,977,225 A | 11/1999 | Scholl |
| 6,046,349 A | 4/2000 | Batz-Sohn et al. |
| 6,127,468 A | 10/2000 | Cruse et al. |
| 6,140,393 A | 10/2000 | Bomai et al. |
| 6,140,524 A | 10/2000 | Ichonoke et al. |
| 6,194,594 B1 | 2/2001 | Gori et al. |
| 6,194,595 B1 | 2/2001 | Michel et al. |
| 6,204,339 B1 | 3/2001 | Waldman et al. |
| 6,211,345 B1 | 4/2001 | Weller |
| 6,268,421 B1 | 7/2001 | Dittrich et al. |
| 6,359,046 B1 | 3/2002 | Cruse |
| 6,407,153 B1 | 6/2002 | Von Hellens |
| 6,414,061 B1 | 7/2002 | Cruse et al. |
| 6,420,488 B1 | 7/2002 | Penot |
| 6,518,367 B1 | 2/2003 | Yatsuyanagi et al. |
| 6,528,673 B2 | 3/2003 | Cruse et al. |
| 6,608,125 B2 | 8/2003 | Cruse et al. |
| 6,649,684 B1 | 11/2003 | Okel |
| 6,683,135 B2 | 1/2004 | Cruse et al. |
| 6,759,545 B2 | 7/2004 | Yanagisawa et al. |
| 6,777,569 B1 | 8/2004 | Westmeyer et al. |
| 6,849,754 B2 | 2/2005 | Deschler et al. |
| 6,890,981 B1 | 5/2005 | Luginsland |
| 6,984,689 B2 | 1/2006 | Penot et al. |
| 6,984,711 B2 | 1/2006 | Wonmun et al. |
| 7,041,843 B2 | 5/2006 | Yanagisawa et al. |
| 7,122,590 B2 | 10/2006 | Cruse et al. |
| 7,138,537 B2 | 11/2006 | Cruse et al. |
| 7,166,735 B2 | 1/2007 | Yanagisawa et al. |
| 7,186,768 B2 | 3/2007 | Korth et al. |
| 7,199,256 B2 | 4/2007 | Yanagisawa et al. |
| 7,217,751 B2 | 5/2007 | Durel et al. |
| 7,288,667 B2 | 10/2007 | Yanagisawa |
| 7,301,042 B2 | 11/2007 | Cruse |
| 7,307,121 B2 | 12/2007 | Zhang et al. |
| 7,309,797 B2 | 12/2007 | Yanagisawa |
| 7,355,059 B2 | 4/2008 | Yanagisawa |
| 7,368,588 B2 | 5/2008 | Yanagisawa |
| 2002/0002220 A1 | 1/2002 | Reedy et al. |
| 2002/0055564 A1 | 5/2002 | Cruse et al. |
| 2003/0130388 A1 | 7/2003 | Luglnsland et al. |
| 2003/0199619 A1 | 10/2003 | Cruse |
| 2003/0200900 A1 | 10/2003 | Korth et al. |
| 2003/0225195 A1 | 12/2003 | Cruse et al. |
| 2004/0143037 A1 | 7/2004 | Chang et al. |
| 2004/0147651 A1 | 7/2004 | Barruel et al. |
| 2004/0210001 A1 | 10/2004 | Cruse et al. |
| 2004/0220307 A1 | 11/2004 | Wu |
| 2005/0009955 A1 | 1/2005 | Cohen |
| 2005/0027060 A1 | 2/2005 | Yagi et al. |
| 2005/0176861 A1 | 8/2005 | Nakayama et al. |
| 2005/0245753 A1 | 11/2005 | Cruse et al. |
| 2005/0245754 A1 | 11/2005 | Glatzer et al. |
| 2006/0036034 A1 | 2/2006 | Chaves et al. |
| 2006/0106143 A1 | 5/2006 | Lin et al. |
| 2006/0177657 A1 | 8/2006 | Weller |
| 2006/0205907 A1 | 9/2006 | Guyer |
| 2006/0235236 A1 | 10/2006 | Simandan |
| 2006/0281841 A1 | 12/2006 | Weller et al. |
| 2007/0037915 A1 | 2/2007 | Masumoto |
| 2007/0083011 A1* | 4/2007 | Pohl et al. .......... 525/326.1 |
| 2007/0135572 A1 | 6/2007 | Woller |
| 2007/0197812 A1 | 8/2007 | Chaves et al. |
| 2007/0197813 A1 | 8/2007 | Chaves et al. |
| 2008/0027162 A1 | 1/2008 | Hua et al. |
| 2008/0161452 A1 | 7/2008 | York et al. |
| 2008/0161460 A1 | 7/2008 | York et al. |
| 2008/0161461 A1 | 7/2008 | Cruse et al. |
| 2008/0161462 A1 | 7/2008 | York et al. |
| 2008/0161475 A1 | 7/2008 | York et al. |
| 2008/0161477 A1 | 7/2008 | Cruse et al. |
| 2008/0161483 A1 | 7/2008 | Cruse et al. |
| 2008/0161486 A1 | 7/2008 | York et al. |
| 2008/0161590 A1 | 7/2008 | Cruse et al. |

FOREIGN PATENT DOCUMENTS

| | | |
|---|---|---|
| CA | 1018991 | 10/1977 |
| CA | 2103653 | 2/1994 |
| CA | 2186060 | 3/1997 |
| CA | 2231302 | 9/1998 |
| CA | 2146333 | 5/2010 |
| DE | 2141159 | 3/1973 |
| DE | 2141160 | 3/1973 |
| DE | 2255577 | 6/1974 |
| DE | 2360471 | 6/1975 |
| DE | 2405758 | 8/1975 |
| DE | 2536674 | 2/1977 |
| DE | 2747277 | 4/1979 |
| DE | 2819638 | 11/1979 |
| DE | 2848559 | 5/1980 |
| DE | 2856229 | 7/1980 |
| DE | 3028365 | 2/1982 |
| DE | 3305373 | 8/1984 |
| DE | 3314742 | 10/1984 |
| DE | 3311340 | 11/1984 |
| DE | 3437473 | 4/1986 |
| DE | 4023537 | 1/1992 |
| DE | 4119959 | 12/1992 |
| DE | 4128203 | 5/1993 |
| DE | 4236218 | 8/1993 |
| DE | 4225978 | 4/1994 |
| DE | 43088311 | 9/1994 |
| DE | 19702046 | 1/1998 |
| DE | 19819373 | 11/1999 |
| DE | 10222509 | 3/2003 |
| DE | 4004781 | 5/2010 |
| EP | 0784072 | 7/1977 |
| EP | 0845493 | 6/1996 |
| EP | 0764687 | 3/1997 |
| EP | 0795577 | 9/1997 |
| EP | 0680997 | 9/1998 |
| EP | 0864605 | 9/1998 |
| EP | 0732362 | 6/1999 |
| EP | 0773224 | 12/2001 |
| EP | 0631982 | 1/2002 |
| EP | 0955302 | 6/2002 |
| EP | 0919559 | 11/2002 |
| EP | 0848006 | 8/2003 |
| EP | 1491545 | 12/2004 |
| EP | 0738748 | 8/2005 |
| EP | 1270657 | 3/2006 |
| EP | 1634726 | 3/2006 |
| EP | 1514892 | 7/2006 |
| EP | 1714984 | 10/2006 |
| FR | 2804104 | 7/2001 |
| GB | 1439247 | 6/1976 |
| GB | 2259303 | 10/1993 |
| GB | 2004-104455 | 4/2006 |
| GB | 2103653 | 11/2010 |
| JP | 63-270751 | 8/1988 |
| JP | 002479646 | 12/1996 |
| JP | 8319225 | 12/1996 |
| JP | 2000-154380 | 6/2000 |
| JP | 2001-226383 | 8/2001 |
| JP | 2001-226532 | 8/2001 |
| JP | 2006-104455 | 4/2004 |

(56) References Cited

FOREIGN PATENT DOCUMENTS

| | | |
|---|---|---|
| JP | 2005-263127 | 9/2005 |
| JP | 2005-263998 | 9/2005 |
| JP | 2005-263999 | 9/2005 |
| JP | 2005-272630 | 10/2005 |
| JP | 2005-281621 | 10/2005 |
| JP | 2005-320317 | 11/2005 |
| JP | 2005-320374 | 11/2005 |
| JP | 2006-28253 | 2/2006 |
| JP | 2006-28430 | 2/2006 |
| JP | 2008-28245 | 2/2006 |
| JP | 2006-213777 | 8/2006 |
| JP | 2006-213803 | 8/2006 |
| JP | 2006-225448 | 8/2006 |
| JP | 2006-232881 | 9/2006 |
| JP | 2006-232916 | 9/2006 |
| JP | 2006-232917 | 9/2006 |
| JP | 2007-51169 | 3/2007 |
| JP | 002479812 | 11/2007 |
| KR | 10-2005-0025817 | 3/2005 |
| WO | 98/53004 | 11/1998 |
| WO | 99/07713 | 2/1999 |
| WO | 99/09036 | 2/1999 |
| WO | 00/05300 | 2/2000 |
| WO | 00/53671 | 9/2000 |
| WO | 01/46202 | 6/2001 |
| WO | 02/20534 | 3/2002 |
| WO | 02/48256 | 6/2002 |
| WO | 03/035252 | 5/2003 |
| WO | 2004000930 | 12/2003 |
| WO | 2004/005395 | 1/2004 |
| WO | 2005/007660 | 1/2005 |
| WO | 2005/007661 | 1/2005 |
| WO | 2006/113122 | 10/2006 |
| WO | 2007/039416 | 4/2007 |
| WO | 2007/068555 | 6/2007 |
| WO | 2007/085521 | 8/2007 |
| WO | 2007/132909 | 11/2007 |
| WO | 2008/074567 | 6/2008 |

* cited by examiner

BLOCKED MERCAPTOSILANE COUPLING AGENTS, PROCESS FOR MAKING THE USES IN RUBBER

The present application is a continuation of copending U.S. patent application Ser. No. 12/820,198 filed on Jun. 22, 2010, which is a divisional of U.S. patent application Ser. No. 11/647,780 filed on Dec. 22, 2006 and now issued as U.S. Pat. No. 7,781,606, to which priority is claimed and which is herein incorporated by reference in its entirety.

The present application is directed to an invention which was developed pursuant to a joint research agreement wherein the meaning of 35 U.S.C. §103(c). The joint research agreement dated May 7, 2001 as amended, between Continental AG, and General Electric Company, on behalf of GE Advanced Materials, Silicones Division, now Momentive Performance Materials Inc.

CROSS-REFERENCE TO RELATED APPLICATIONS

The present application is related to the following applications, filed on even date herewith, with the disclosures of each the applications being incorporated by reference herein in their entireties:

Application Ser. No. 11/617,683, filed Dec. 28, 2006, entitled "Tire Compositions And Components Containing Silated Cyclic Core Polysulfides".

Application Ser. No. 11/617,649, filed Dec. 28, 2006, entitled "Tire Compositions And Components Containing Free-Flowing Filler Compositions".

Application Ser. No. 11/617,678 filed Dec. 28, 2006, entitled "Tire Compositions And Components Containing Free-Flowing Filler Compositions".

Application Ser. No. 11/617,663, filed Dec. 28, 2006, entitled "Tire Compositions And Components Containing Silated Core Polysulfides".

Application Ser. No. 11/617,659, filed Dec. 28, 2006, entitled "Tire Compositions And Components Containing Blocked Mercaptosilane Coupling Agent".

Application Ser. No. 11/647,901, filed Dec. 28, 2006, entitled "Silated Cyclic Core Polysulfides, Their Preparation And Use In Filled Elastomer Compositions".

Application Ser. No. 11/648,460, filed Dec. 28, 2006, entitled "Free-Flowing Filler Composition And Rubber Composition Containing Same".

Application Ser. No. 11/647,903, filed Dec. 28, 2006, entitled "Free-Flowing Filler Composition And Rubber Composition Containing Same".

Application Ser. No. 11/648,287, filed Dec. 28, 2006, entitled "Silated Core Polysulfides, Their Preparation And Use In Filled Elastomer Compositions".

BACKGROUND OF THE INVENTION

This invention relates to sulfur silane coupling agents containing multiple blocked mercapto groups which are latent, that is, they are in a state of reduced activity until such a time as one finds it useful to activate them. The invention also relates to the manufacture of mineral filled elastomers, rubbers and inorganic fillers comprising these silane coupling agents, as well as to the manufacture of the silanes.

The majority of art dealing with of sulfur-containing coupling agents in mineral filled elastomers involves silanes containing one or more of the following chemical bond types:

S—H (mercapto), S—S (disulfide or polysulfide), C=S (thiocarbonyl) or C(=O)S (thioester). Mercaptosilanes have high chemical reactivity with organic polymers used in mineral filled elastomers and therefore effect coupling at substantially reduced loadings. However, these chemical bonds between the coupling agent and the organic polymer are weaker than the carbon-carbon bonds of the organic polymer. Under high stress and/or high frequency use conditions, these chemical bonds are susceptible to breakage and, therefore, loss of coupling between the organic polymer and the coupling agent. The loss of coupling may contribute to the wear and to the degradation of other elastomeric physical properties. The high chemical reactivity of mercaptosilane coupling agents with organic polymers also leads to unacceptably high viscosities during processing and premature curing (scorch). Their undesirability is aggravated by their odor. As a result, other, less reactive coupling agents such as the coupling agents that contain the S—S (disulfide and polysulfide), C=S (thiocarbonyl) or C(=O)S (thioester) functional groups are used. Because these silane coupling agents are less reactive with the organic polymers, they require higher use levels and often do not achieve the same level of bonding. Similar to the mercaptosilane coupling agents, these sulfur silanes are bonded to the organic polymer through a C—S bond.

The prior art discloses acylthioalkyl silanes, such as $CH_3C(=O)S(CH_2)_{1-3}Si(OR)_3$ (M. G. Voronkov et al. in *Inst. Org. Khim.*, Irkutsk, Russia) and $HOC(=O)CH_2CH_2C(=O)S(CH_2)_3Si(OC_2H_5)_3$ (U.S. Pat. No. 3,922,436 to R. Bell et al.). Takeshita and Sugawara disclosed in Japanese Patent JP 63270751 A2 the use of compounds represented by the general formula $CH_2=C(CH_3)C(=O)S(CH_2)_{1-6}Si(OCH_3)_3$ in tire tread compositions; but these compounds are not desirable because the unsaturation α,β to the carbonyl group of the thioester has the undesirable potential to polymerize during the compounding process or during storage. Prior art by Yves Bomal and Olivier Durel in Australian Patent AU-A-10082/97 discloses the use in rubber of silanes of the structure represented by $R^1{}_nX_{3-n}Si\text{-}(Alk)_m(Ar)_p\text{—}S(C=O)\text{—}R$ (Formula 1P) where $R^1$ is phenyl or alkyl; X is halogen, alkoxy, cycloalkoxy, acyloxy, or OH; Alk is alkyl; Ar is aryl; R is alkyl, alkenyl, or aryl; n is 0 to 2; and m and p are each 0 or 1, but not both zero. This prior art, however, stipulates that compositions of the structures of Formula (1P) must be used in conjunction with functionalized siloxanes. The prior art does not disclose or suggest the use of compounds of Formula (1P) as latent mercaptosilane coupling agents, nor does it disclose or suggest the use of these compounds in any way that would give rise to the advantages of using them as a source of latent mercaptosilane. In addition, these patents do not describe coupling agent that have multiple thioester groups in the appropriate stereochemical configuration to foster multiple linkages to the organic polymer.

U.S. Pat. Nos. 6,608,125; 6,683,135; 620,439; 6,127,468; 6,777,569; 6,528,673 and 6,649,684, US Patent Publication Nos. US20050009955A1, 20040220307A1, 2003020900A1, 20030130388A1, and application Ser. Nos. 11/105,916 and 10/128,804, and European patent application EP1270657A1 teach the use of blocked mercaptosilanes of the structure represented by $[[(ROC(=O))_p\text{-}(G)_j]_k\text{-}Y\text{—}S]_r\text{-}G\text{-}(SiX_3)_s$, where Y is a polyvalent blocking group $(Q)_zA(=E)$ and r is an integer 1 to 3 in rubber compounds and s is preferably 1 to 3, in rubber master batches and as a surface treatment for mineral fillers and how to manufacture the silane. Although these patents and patent applications disclose structures that possess more than one blocked mercapto group, i.e. r=2 or 3, they do not teach the specific stereochemical configurations of the polyvalent G structure between the silicon atom and the organofunctional group necessary to achieve the efficient multiple bonding between the coupling agent and the organic polymer.

U.S. Pat. No. 4,519,430 to Ahmad et al. and U.S. Pat. No. 4,184,998 to Shippy et al. disclose the blocking of a mercaptosilane with an isocyanate to form a solid which is added to a tire composition, which mercaptan reacts into the tire during heating, which could happen at any time during processing since this is a thermal mechanism. The purpose of this silane is to avoid the sulfur smell of the mercaptosilane, not to improve the processing of the tire. Moreover, the isocyanate used has toxicity issues when used to make the silane and when released during rubber processing.

U.S. Pat. No. 3,957,718 to Porchet et al. discloses compositions containing silica, phenoplasts or aminoplasts, and silanes, such as xanthates, thioxanthates, and dithiocarbamates; however, the prior art does not disclose or suggest the use of these silanes as latent mercaptosilane coupling agents, nor does it suggest or disclose the advantage of using them as a source of latent mercaptosilane.

U.S. Pat. Nos. 6,359,046; 5,663,226; 5,780,531; 5,827,912; 5,977,225; 4,709,065; 6,759,545 and WO 2004000930A1 disclose a class of polysulfide silane coupling agents that contain more than one S—S (disulfide or polysulfide) functional groups per molecule. However, the multiple S—S linkages are achieved by separating the functional groups with an organic hydrocarbon radical. In use, these S—S groups decompose to form sulfur radicals that couple to the polymer, but generate species that contain only one sulfur reactive group per silicon atom. Dittrich, et al. in U.S. Pat. Nos. 5,110,969 and 6,268,421 and Weller, et al., overcame this feature. They disclosed structures that contain more than one sulfur functional group directly attached to silicon atom through a cyclic hydrocarbon radical. The multiple S—S groups were bonded to adjacent carbon atoms and the silicon atoms were directly attached to the rings through hydrosilation of the alkoxysilane to a vinyl containing cyclic hydrocarbons. However, these compounds contained rings of S—S and carbon atoms or were polymeric materials wherein the silyl containing hydrocarbon radicals were connected through S—S groups. These cyclic or polymeric coupling agents were rendered less reactive with the organic polymers because they contained S—S groups attached directly to secondary carbons. The attachment of the S—S containing group to secondary carbon atoms sterically hinder the reaction of the S—S groups and inhibit their reactions with the organic polymers.

Therefore, a need exists for latent coupling agents that have low reactivity to affect processing of the mineral filled elastomers or rubbers without scorch and can be activated at the desired time to form multiple linkages with the organic polymer. These multiple linkages provide sufficient bonding so that the loss of coupling between the rubber and coupling agent is minimized during high stress or frequency use conditions, such as is experienced by tires, without exhibiting the disadvantages such as described herein.

BRIEF DESCRIPTION OF THE INVENTION

The present invention is directed to the composition, manufacture and use of blocked mercaptosilane derivatives in which more than one mercapto group is directly linked to the silicon atom through carbon-carbon bonds and in which the mercapto group is blocked ("blocked mercaptosilanes"), i.e., the mercapto hydrogen atom is replaced by another group (hereafter referred to as "blocking group"). Specifically, the silanes of the present invention are blocked mercaptosilanes in which the blocking group contains an unsaturated heteroatom or carbon chemically bound directly to sulfur via a single bond. The use of these silanes in the manufacture of inorganic filled rubbers is taught wherein they are deblocked by the use of a deblocking agent during the manufacturing process. The uses of these silanes in the preparation of masterbatches and treated fillers and the manufacture of such silanes are taught as well.

More particularly, the present invention is directed to blocked mercaptosilane compositions comprising at least one component having the chemical structure in formula (1) consisting of:

$$[R_k\text{—}Y\text{—}S(CH_2)_n]_r\text{-}G\text{-}(CH_2)_m\text{—}(SiX^1X^2X^3) \quad (1)$$

wherein
each occurrence of Y is a polyvalent species $(Q)_zA(=E)$, preferably selected from the group consisting of

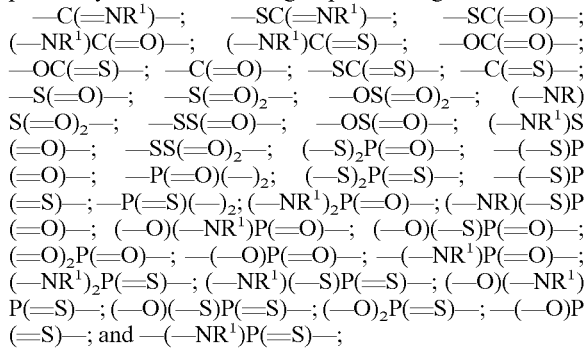

wherein each atom (A) attached to the unsaturated heteroatom (E) is attached to the sulfur, which in turn is linked via a group —$(CH_2)_nG(CH_2)_m$— to the silicon atom;

each occurrence of R is chosen independently from hydrogen, straight, cyclic, or branched alkyl, alkenyl groups, aryl groups, and aralkyl groups, with each R containing up to about 18 carbon atoms;

each occurrence of $R^1$ is chosen independently from hydrogen, alkyl, alkenyl, aryl or aralkyl groups with each $R^1$ containing up to about 18 carbon atoms;

each occurrence of G is chosen independently from a group consisting of a trivalent or polyvalent hydrocarbon group of 3 to 30 carbon atoms derived by substitution of alkane, alkene or aralkane or a trivalent or polyvalent heterocarbon group of 2 to 29 carbon atoms with the proviso that G contains a cyclic structure (ring);

each occurrence of $X^1$ is independently selected from the set of hydrolysable groups group consisting of —Cl, —Br, $R^1$O—, $R^1$C(=O)O—, $R^1{}_2$C=NO—, $R^1{}_2$NO— or $R_2$N—, wherein each $R^1$ is as above;

each occurrence of $X^2$ and $X^3$ are independently chosen from the group consisting of the members listed for $R^1$ and $X^1$;

each occurrence of Q is selected independently from oxygen, sulfur, or (—NR—);

each occurrence of A is selected independently from carbon, sulfur, phosphorus, or sulfonyl;

each occurrence of E is selected independently from oxygen, sulfur, or $NR^1$;

k is 1 to 2; m=1 to 5; n=1 to 5; r is 2 to 4; z is 0 to 2; with the proviso that if A is phosphorus, then k is 2.

In another embodiment, the present invention is directed to a process for the preparation of the blocked mercaptosilane comprising reacting a thioacid with a silylated hydrocarbon containing r terminal carbon-carbon double bonds.

In another embodiment, the present invention is directed to a process for the preparation of the blocked mercaptosilane comprising reacting a salt of a thioacid with a silane containing r haloalkyl groups, wherein the halogen is attached to a primary carbon atom.

In still another embodiment, the present invention is directed to filled elastomer or rubber compound comprising the blocked mercaptosilanes of the present invention.

In another embodiment, the present invention is directed to a treated filler in which the treated filler comprises the blocked mercaptosilane of the present invention.

DETAILED DESCRIPTION OF THE INVENTION

Silane Structures

The novel blocked mercaptosilanes of the present invention can be represented by the Formula (1):

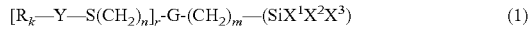

$$[R_k-Y-S(CH_2)_n]_r-G-(CH_2)_m-(SiX^1X^2X^3) \quad (1)$$

wherein
each occurrence of Y is a polyvalent species $(Q)_zA(=E)$, preferably selected from the group consisting of
—C(=NR$^1$)—; —SC(=NR$^1$)—; —SC(=O)—; (—NR$^1$)C(=O)—; (—NR$^1$)C(=S)—; —OC(=O)—; —OC(=S)—; —C(=O)—; —SC(=S)—; —C(=S)—; —S(=O)—; —S(=O)$_2$—; —OS(=O)$_2$—; (—NR) S(=O)$_2$—; —SS(=O)—; —OS(=O)—; (—NR$^1$)S (=O)—; —SS(=O)$_2$—; (—S)$_2$P(=O)—; —(—S)P) (=O)—; —P(=O)(—)$_2$; (—S)$_2$P(=S)—; —(—S)P (=S)—; —P(=S)(—)$_2$; (—NR$^1$)$_2$P(=O)—; (—NR)(—S)P (=O)—; (—O)(—NR$^1$)P(=O)—; (—O)(—S)P(=O)—; (—O)$_2$P(=O)—; —(—O)P(=O)—; —(—NR$^1$)P(=O)—; (—NR$^1$)$_2$P(=S)—; (—NR$^1$)(—S)P(=S)—; (—O)(—NR$^1$) P(=S)—; (—O)(—S)P(=S)—; (—O)$_2$P(=S)—; —(—O)P (=S)—; and —(—NR$^1$)P(=S)—;

wherein each atom (A) attached to the unsaturated heteroatom (E) is attached to the sulfur, which in turn is linked via a group —(CH$_2$)$_n$G(CH$_2$)$_m$— to the silicon atom;

each occurrence of R is chosen independently from hydrogen, straight, cyclic, or branched alkyl, alkenyl groups, aryl groups, and aralkyl groups, with each R containing from 1 to 18 carbon atoms;

each occurrence of R$^1$ is chosen independently from hydrogen, alkyl, alkenyl, aryl or aralkyl groups with each R$^1$ containing from 1 to 18 carbon atoms;

each occurrence of G is chosen independently form a group consisting of a trivalent or polyvalent hydrocarbon group of 3 to 30 carbon atoms derived by substitution of alkane, alkene or aralkane or a trivalent or polyvalent heterocarbon group of 2 to 29 carbon atoms with the proviso that G contains a cyclic structure (ring);

each occurrence of X$^1$ is independently selected from the set of hydrolysable groups consisting of —Cl, —Br, R$^1$O—, R$^1$C(=O)O—, R$^1$$_2$C=NO—, R$^1$$_2$NO— or R$_2$N—, wherein each R$^1$ is as above;

each occurrence of X$^2$ and X$^3$ are independently chosen from the group consisting of the members listed for R$^1$ and X$^1$;

each occurrence of Q is selected independently from oxygen, sulfur, or (—NR—);

each occurrence of A is selected independently from carbon, sulfur, phosphorus, or sulfonyl;

each occurrence of E is selected independently from oxygen, sulfur, or NR$^1$;

k is 1 to 2; m=1 to 5; n=1 to 5; r is 2 to 4; z is 0 to 2; with the proviso that if A is phosphorus, then k is 2.

The term, "heterocarbon", as used herein, refers to any hydrocarbon structure in which the carbon-carbon bonding in the backbone is interrupted by bonding to atoms of nitrogen, and/or oxygen; or in which the carbon-carbon bonding in the backbone is interrupted by bonding to groups of atoms containing nitrogen and/or oxygen, such as cyanurate (C$_3$N$_3$). Heterocarbon groups also refer to any hydrocarbon in which a hydrogen or two or more hydrogens bonded to carbon are replace with a oxygen or nitrogen atom, such as a primary amine (—NH$_2$), and oxo (=O). Thus, G includes, but is not limited to branched, straight-chain hydrocarbon containing at least one ring structure, cyclic, and/or polycyclic aliphatic hydrocarbons, optionally containing ether functionality via oxygen atoms each of which is bound to two separate carbon atoms, tertiary amine functionality via nitrogen atoms each of which is bound to three separate carbon atoms, and/or cyanurate (C$_3$N$_3$) groups; aromatic hydrocarbons; and arenes derived by substitution of the aforementioned aromatics with branched or straight chain alkyl, alkenyl, alkynyl, aryl and/or aralkyl groups.

As used herein, "alkyl" includes straight, branched and cyclic alkyl groups; "alkenyl" includes any straight, branched, or cyclic alkenyl group containing one or more carbon-carbon double bonds, where the point of substitution can be either at a carbon-carbon double bond or elsewhere in the group; and "alkynyl" includes any straight, branched, or cyclic alkynyl group containing one or more carbon-carbon triple bonds and optionally also one or more carbon-carbon double bonds as well, where the point of substitution can be either at a carbon-carbon triple bond, a carbon-carbon double bond, or elsewhere in the group. Specific examples of alkyls include methyl, ethyl, propyl, isobutyl. Specific examples of alkenyls include vinyl, propenyl, allyl, methallyl, ethylidenyl norbornane, ethylidene norbornyl, ethylidenyl norbornene, and ethylidene norbornenyl. Specific examples of alkynyls include acetylenyl, propargyl, and methylacetylenyl.

As used herein, "aryl" includes any aromatic hydrocarbon from which one hydrogen atom has been removed; "aralkyl" includes any of the aforementioned alkyl groups in which one or more hydrogen atoms have been substituted by the same number of like and/or different aryl (as defined herein) substituents; and "arenyl" includes any of the aforementioned aryl groups in which one or more hydrogen atoms have been substituted by the same number of like and/or different alkyl (as defined herein) substituents. Specific examples of aryls include phenyl and naphthalenyl. Specific examples of aralkyls include benzyl and phenethyl. Specific examples of arenyls include tolyl and xylyl.

As used herein, "cyclic alkyl", "cyclic alkenyl", and cyclic alkynyl also include bicyclic, tricyclic, and higher cyclic structures, as well as the aforementioned cyclic structures further substituted with alkyl, alkenyl, and/or alkynyl groups. Representative examples include norbornyl, norbornenyl, ethylnorbornyl, ethylnorbornenyl, ethylcyclohexyl, ethylcyclohexenyl, cyclohexylcyclohexyl, and cyclododecatrienyl.

Representative examples of the functional groups (—YS—) present in the silanes of the present invention include thiocarboxylate ester, —C(=O)S— (any silane with this functional group is a "thiocarboxylate ester silane"); dithiocarboxylate, —C(=S)S— (any silane with this functional group is a "dithiocarboxylate ester silane"); thiocarbonate ester, —OC(=O)S— (any silane with this functional group is a "thiocarbonate ester silane"); dithiocarbonate ester, —SC(=O)S— and —OC(=S)S— (any silane with this functional groups is a "dithiocarbonate ester silane"); trithiocarbonate ester, —SC(=S)S— (any silane with this functional group is a "trithiocarbonate ester silane"); dithiocarbamate ester, (—N—)C(=S)S— (any silane with this functional group is a "dithiocarbamate ester silane"); thiosulfonate ester, —S(=O)$_2$S— (any silane with this functional group is a "thiosulfonate ester silane"); thiosulfate ester, —OS($=$O)$_2$S— (any silane with this functional group is a "thiosulfate ester silane"); thiosulfamate ester, (—N—)S($=$O)$_2$S— (any silane with this functional group is a "thiosulfamate ester silane"); thiosulfinate ester, —S($=$O)S— (any silane with this functional group is a "thiosulfinate ester silane"); thiosulfite ester, —OS($=$O)S— (any silane with this functional group is a "thiosulfite ester silane"); thiosulfimate ester, (—N—)S($=$O)S— (any silane with this functional group is a "thiosulfimate ester silane"); thiophosphate ester, P($=$O)(O—)$_2$(S—) (any silane with this functional group is a "thiophosphate ester silane"); dithiophosphate ester, P($=$O)(O—)(S—)$_2$ or P($=$S)(O—)$_2$(S—) (any silane with this functional group is a "dithiophosphate ester silane"); trithiophosphate ester, P($=$O)(S—)$_3$ or P($=$S)(O—)(S—)$_2$ (any silane with this functional group is a "trithiophosphate ester silane"); tetrathiophosphate ester P($=$S)(S—)$_3$ (any silane with this functional group is a "tetrathiophosphate ester silane"); thiophosphamate ester, —P($=$O)(—N—)(S—) (any silane with this functional group is a "thiophosphamate ester silane"); dithiophosphamate ester, —P($=$S)(—N—)(S—) (any silane with this functional group is a "dithiophosphamate ester silane"); thiophosphoramidate ester, (—N—)P($=$O)(O—)(S—) (any silane with this functional group is a "thiophosphoramidate ester silane"); dithiophosphoramidate ester, (—N—)P($=$O)(S—)$_2$ or (—N—)P($=$S)(O—)(S—) (any silane with this functional group is a "dithiophosphoramidate ester silane"); trithiophosphoramidate ester, (—N—)P($=$S)(S—)$_2$ (any silane with this functional group is a "trithiophosphoramidate ester silane").

Representative examples of $X^1$ include methoxy, ethoxy, propoxy, isopropoxy, butoxy, phenoxy, benzyloxy, hydroxy, chloro, and acetoxy. Representative examples of $X^2$ and $X^3$ include the representative examples listed above for $X^1$ as well as methyl, ethyl, propyl, isopropyl, sec-butyl, phenyl, vinyl, cyclohexyl, and higher straight-chain alkyl, such as butyl, hexyl, octyl, lauryl, and octadecyl.

Representative examples of trisubstutitued G include any of the structures derivable from vinylnorbornene and vinylcyclohexene, such as —CH$_2$CH$_2$-norbornyl=, —CH(CH$_3$)-norbornyl=, —CH$_2$(CH—)-norbornyl-, —CH$_2$CH$_2$-cyclohexyl=, —CH(CH$_3$)-cyclohexyl=, and —CH$_2$(CH—)-cyclohexyl-; any of the structures derivable from limonene, such as —CH$_2$CH(CH$_3$)[(4-methyl-1-C$_6$H$_8$=)CH$_3$], —C(CH$_3$)$_2$[(4-methyl-1-C$_6$H$_8$=)CH$_3$], and —CH$_2$(C—)(CH$_3$)[(4-methyl-1-C$_6$H$_9$—)CH$_3$], where the notation C$_6$H9 denotes isomers of the trisubstituted cyclohexane ring lacking substitution in the 2 position and where C$_6$H$_8$ denotes the 1,4 disubstituted cyclohexene ring; any of the vinyl-containing structures derivable from trivinylcyclohexane, such as —CH$_2$(CH—)(vinylC$_6$H$_9$)CH$_2$CH$_2$— and —CH$_2$(CH—)(vinylC$_6$H$_9$)CH(CH$_3$)—; any of the structures derivable from trivinylcyclohexane, such as (—CH$_2$CH$_2$)$_3$C$_6$H$_9$, (—CH$_2$CH$_2$)$_2$C$_6$H$_9$CH(CH$_3$)—, —CH$_2$CH$_2$C$_6$H$_9$[CH(CH$_3$)—]$_2$, and C$_6$H$_9$[CH(CH$_3$)—]$_3$, where the notation C$_6$H$_9$ denotes any isomer of the trisubstituted cyclohexane ring; any structure derivable by trisubstitution of cyclopentane, tetrahydrocyclopentadiene, cyclohexane, cyclodecane, cyclododecane, any of the cyclododecenes, any of the cyclododecadienes, cycloheptane, any of the cycloheptenes and any of the cycloheptadienes; trisubstituted cyanurate, piperazine, cyclohexanone, and cyclohexenone; and any structure derivable by trisubstituted benzene, tolune, xylene, mesitylene and naphthalene.

Representative examples of tetrasubstituted G include any of the structures derivable from vinylnorbornene or vinylcyclohexene, such as —CH$_2$(CH—)-norbornyl= and —CH$_2$(CH—)-cyclohexyl=; any of the structures derivable from limonene, such —CH$_2$(C—)(CH$_3$)[(4-methyl-1-C$_6$H$_8$=)CH$_3$], where the notation C$_6$H$_8$ denotes the 1,4 disubstituted cyclohexene ring; any of the vinyl-containing structures derivable from trivinylcyclohexane, such as —CH$_2$(CH—)(vinylC$_6$H$_9$)(CH—)CH$_2$—, where the notation C$_6$H$_9$ denotes any isomer of the trisubstituted cyclohexane ring; any of the structures derivable from trivinylcyclohexane, such as —CH$_2$(CH—)C$_6$H$_9$[CH(CH$_3$)—]$_2$, —CH$_2$(CH—)C$_6$H$_9$[CH$_2$CH$_2$—]$_2$, and —CH$_2$(CH—)C$_6$H$_9$[CH(CH$_3$)—][CH$_2$CH$_2$—], where the notation C$_6$H$_9$ denotes any isomer of the trisubstituted cyclohexane ring; and any structure derivable by tetrasubstitution of cyclopentane, tetrahydrocyclopentadiene, cyclohexane, cyclodecane, cyclododecane, any of the cyclododecenes, any of the cyclododecadienes, cycloheptane, any of the cycloheptenes and any of the cycloheptadienes; and any structure derivable by tetrasubstitution of benzene, toluene, xylene, mesitylene and naphthalene.

Representative examples of pentasubstituted G include any of the structures derivable from trivinylcyclohexane, such as —CH$_2$CH$_2$C$_6$H$_9$[(CH—)CH$_2$—]$_2$, —CH(CH$_3$)C$_6$H$_9$[(CH—)CH$_2$—]$_2$, and C$_6$H$_9$[(CH—)CH$_2$—]$_3$, where the notation C$_6$H$_9$ denotes any isomer of the trisubstituted cyclohexane ring, and any structure derivable by pentasubstitution or hexasubstitution of cyclododecane.

Representative examples of R include hydrogen, methyl, ethyl, propyl, isopropyl, butyl, hexyl, 2-ethylhexyl, octyl, dodecyl, octadecyl, cyclohexyl, phenyl, benzyl, phenethyl, methallyl, and allyl.

In another embodiment of the present invention represented by formula (1) wherein each occurrence of Y is a polyvalent species (Q)$_z$A($=$E), each occurrence of Q is independently selected from oxygen, sulfur or NR$^1$, and A is carbon and E is selected independently from oxygen, sulfur or NR$^1$. Representative examples are selected from, but not limited to, the group —C($=$NR)—; —SC($=$NR)—; —NR$^1$C($=$NR$^1$)—; —C($=$O)—; —SC($=$O)—; —OC($=$O)—; —NR$^1$C($=$O)—; and —C($=$S)—; —NR$^1$C($=$S)—; —SC($=$S)—.

In another embodiment of the present invention represented by formula (1) Y is —C($=$O)—.

In another embodiment of the present invention each occurrence of m is 2-4 and n is 1-4.

In another embodiment of the present invention each occurrence of m is 2-4 and n is 2-4.

In another embodiment of the present invention each occurrence of m is 2 and n is 2.

In another embodiment of the present invention each occurrence of G is a substituted hydrocarbon containing at least one ring and from 1 to 18 carbon atoms.

In another embodiment of the present invention each occurrence of G is selected from the group consisting of substituted cyclopentane, cyclohexane, cycloheptane, cyclooctane, cyclododecane and benzene.

In another embodiment of the present invention each occurrence of the R is a straight chain alkyl group from 1 to 8 carbon atoms.

In another embodiment of the present invention each occurrence of the R is selected from the group consisting of hydrogen, methyl, ethyl and propyl.

In still another embodiment of the present invention the sum of the carbon atoms within the R groups within the molecule is from 2 to 16, more preferably 6 to 14. This amount of carbon in the R group facilitates the dispersion of the inorganic filler into the organic polymers and can affect the rate of cure, thereby improving the balance of properties in the cured filled rubber.

In another embodiment of the present invention each occurrence of G is selected from a group consisting of a trisubstituted cyclohexane or benzene, R is a straight chain alkyl group from 1 to 8 carbon atoms, r=2 and m=1 or 2, and n=1 or 2.

Representative examples of the silanes of the present invention include, but are not limited to, 1-(2-triethoxysilylethyl)-3,5-bis-(3-thia-4-oxopentyl)benzene, 1-(2-triethoxysilylethyl)-3,5-bis-(3-thia-4-oxohexyl)benzene, 1-(2-triethoxysilylethyl)-3,5-bis-(3-thia-4-oxoheptyl)benzene, 1-(2-tripropoxysilyhnethyl)-3,5-bis-(3-thia-4-oxopentyl)benzene, 4-(2triethoxysilylethyl)-1,2-bis-(2-thia-3-oxopentyl)benzene, 1-(2-diethoxymethylsilylethyl)-3,5-bis-(3-thia-4-oxopentyl)benzene, 4-(2-dimethylethoxysilylethyl)-1,2-bis-(3-thia-4-oxopentyl)benzene, 4-(2-triethoxysilylethyl)-1,2-bis-(2-thia-3-oxopentyl)cyclohexane, 1-(2-triethoxysilylethyl)-2,4-bis-(2-thia-3-oxopentyl)cyclohexane, 2-(2-triethoxysilylethyl)-1,4-bis-(2-thia-3-oxopentyl)cyclohexane, 4-(2-diethoxymethylsilylethyl)-1,2-bis-(3-thia-4-oxopentyl)cyclohexane, 4-(2-dimethylethoxysilylethyl)-1,2-bis-(3-thia-4-oxopentyl)cyclohexane, 4-(2-triethoxysilylethyl)-1,2-bis-(3-thia-4-oxohexyl)cyclohexane, 1-(2-triethoxysilylethyl)-2,4-bis-(3-thia-4-oxohexyl)cyclohexane, 2-(2-triethoxysilylethyl)-1,4-bis-(3-thia-4-oxohexyl)cyclohexane, 4-(2-triethoxysilylethyl)-1,2-bis-(3-thia-4-oxononyl)cyclohexane, 1-(2-triethoxysilylethyl)-2,4-bis-(3-thia-4-oxononyl)cyclohexane, 2-(2-triethoxysilylethyl)-1,4-bis-(3-thia-4-oxononyl)cyclohexane, 4-(2-triethoxysilylethyl)-1,2-bis-(3-thia-4-oxoundecyl)cyclohexane, 1-(2-triethoxysilylethyl)-2,4-bis-(3-thia-4-oxoundecyl)cyclohexane, 2-(2-triethoxysilylethyl)-1,4-bis-(3-thia-4-oxoundecyl)cyclohexane, 4-(2-dimethylethoxysilylethyl)-1,2-bis-(3-thia-4-oxododecyl)cyclohexane, 4-(2-triethoxysilylethyl)-1,2-bis-(3-thia-4-oxododecyl)cyclohexane, 4-(2-triethoxysilylethyl)-1,2-bis-(3-thia-4-oxo-5-aza-5-methyldodecyl)cyclohexane, (2-triethoxysilylethyl)-1,2-bis-(3,5-dithia-4-oxododecyl)cyclohexane, 1-(2-triethoxysilylethyl)-3,5-bis-(3-thia-4-oxopenyl)mesitylene and 6-(2-triethoxysilylpropyl)-2,2-bis-(3-thia-4-oxopentyl)cyclohexanone, and mixtures thereof.

In another embodiment mixtures of various blocked mercaptosilanes may be used, including wherein synthetic methods result in a distribution of various silanes or where mixes of blocked mercaptosilanes are used for their various blocking or leaving functionalities. Moreover, it is understood that the partial hydrolyzates of these blocked mercaptosilanes (i.e., blocked mercaptosiloxanes) may also be encompassed by the blocked mercaptosilanes herein, in that these partial hydrolyzates will be a side product of most methods of manufacture of the blocked mercaptosilane or can occur upon storage of the blocked mercaptosilane, especially in humid conditions.

In still another embodiment the silane, if liquid, may be loaded on a carrier, such as a porous polymer, carbon black, siliceous filler, or silica so that it is in solid form for delivery to the rubber. The silane can react with the surface groups of the siliceous filler or silica, especially if the silane and filler mixture is heated to about 50 to 150 degrees C. at atmospheric or reduced pressures.

Manufacture of Silanes

An embodiment of the present invention includes methods for the preparation of blocked mercaptosilanes which can involve direct incorporation of the thioester group into a silane by addition of the thioacid across a carbon-carbon double bond. The reaction is the free radical addition of a thioacid across a carbon-carbon double bond of an alkene-functional silane, catalyzed by UV light, heat, or the appropriate free radical initiator wherein, if the thioacid is a thiocarboxylic acid, the two reagents are brought into contact with each other in such a way as to ensure that whichever reagent is added to the other is reacted substantially before the addition proceeds. The reaction can be carried out by heating or refluxing a mixture of the alkene-functional silane and the thioacid. Aspects have been disclosed previously in U.S. Pat. No. 3,692,812 and by G. A. Gomowicz et al., in *J. Org. Chem.* (1968), 33(7), 2918-24. The uncatalyzed reaction can occur at temperatures as low as 105° C., but often fails. The probability of success increases with temperature and becomes high when the temperature exceeds 160° C. The reaction may be made reliable and the reaction brought largely to completion by using UV radiation or a catalyst. With a catalyst, the reaction can be made to occur at temperatures below 90° C. Appropriate catalysts are free radical initiators, e.g., air, peroxides, preferably organic peroxides, and azo compounds. Examples of peroxide initiators include peracids, such as perbenzoic and peracetic acids; esters of peracids; hydroperoxides, such as t-butyl hydroperoxide; peroxides, such as di-t-butyl peroxide; and peroxy-acetals and ketals, such as 1,1-bis(t-butylperoxy)cyclohexane, or any other peroxide. Examples of azo initiators include azobisisobutyronitrile (AIBN), 1,1-azobis(cyclohexanecarbonitrile) (VAZO, DuPont product); and azo-tert-butane. The reaction can be run by heating a mixture of the alkene-functional silane and the thioacid with the catalyst. It is preferable for the overall reaction to be run on an equimolar or near equimolar basis to get the highest conversions. The reaction is sufficiently exothermic that it tends to lead to a rapid temperature increase to reflux followed by a vigorous reflux as the reaction initiates and continues rapidly. This vigorous reaction can lead to hazardous boil-avers for larger quantities. Side reactions, contamination, and loss in yield can result as well from uncontrolled reactions. The reaction can be controlled effectively by adding partial quantities of one reagent to the reaction mixture, initiating the reaction with the catalyst, allowing the reaction to run its course largely to completion, and then adding the remains of the reagent, either as a single addition or as multiple additives. The initial concentrations and rate of addition and number of subsequent additions of the deficient reagent depend on the type and amount of catalyst used, the scale of the reaction, the nature of the starting materials, and the ability of the apparatus to absorb and dissipate heat. A second way of controlling the reaction would involve the continuous addition of one reagent to the other with concomitant continuous addition of catalyst. Whether continuous or sequential addition is used, the catalyst can be added alone and/or preblended with one or both reagents or combinations thereof. Two methods are preferred for reactions involving thioacid, such as thiocarboxylic acid, and alkene-functional silanes containing terminal carbon-carbon double bonds. The first involves initially bringing the alkene-functional silane to a temperature of 160° to 180° C., or to reflux, whichever temperature is lower. The first portion of thioacid is added at a rate as to maintain up to a vigorous, but controlled, reflux. For alkene-functional silanes with boiling points above 100° to 120° C., this reflux results largely from the relatively low boiling point of thioacid (88° to 92° C., depending on purity) relative to the temperature of the alkene-functional silane. At the completion of the addition, the reflux rate rapidly subsides. It often accelerates again within several minutes, especially if an alkene-functional silane with a boiling point above 120° C. is used, as the reaction initiates. If it does not initiate within 10 to 15 minutes, initiation can be brought about by addition of catalyst. The preferred catalyst is di-t-butyl peroxide. The appropriate quantity of catalyst is from 0.2 to 2 percent, preferably from 0.5 to 1 percent, of the total mass of mixture to which the catalyst is added. The reaction typically initiates within a few minutes as evidenced by an increase in reflux rate. The reflux temperature gradually increases as the reaction proceeds. Then the next portion of thioacid is added, and the aforementioned sequence of steps is repeated. The preferred number of thioacid additions for total reaction quantities of about one to about four kilograms is two, with about one-third of the total thioacid used in the first addition and the remainder in the second. For total quantities in the range of about four to ten kilograms, a total of three thioacid additions is preferred, the distribution being approximately 20 percent of the total used in the first addition, approximately 30 percent in the second addition, and the remainder in the third addition. For larger scales involving thioacid and alkene-functional silanes, it is preferable to use more than a total of three thioacid additions and, more preferably, to add the reagents in the reverse order. Initially, the total quantity of thioacid is brought to reflux. This is followed by continuous addition of the alkene-functional silane to the thioacid at such a rate as to bring about a smooth but vigorous reaction rate. The catalyst, preferably di-t-butylperoxide, can be added in small portions during the course of the reaction or as a continuous flow. It is best to accelerate the rate of catalyst addition as the reaction proceeds to completion to obtain the highest yields of product for the lowest amount of catalyst required. The total quantity of catalyst used should be 0.5 to 2 percent of the total mass of reagents used. Whichever method is used, the reaction is followed up by a vacuum stripping process to remove volatiles and unreacted thioacid and silane. The product may be purified by distillation.

In another embodiment of the present invention the reaction is between an alkali metal salt of a thioacid with a haloalkylsilane. The first step involves preparation of a salt of the thioacid. Alkali metal derivatives are preferred, with the sodium derivative being most preferred. These salts would be prepared as solutions in solvents in which the salt is appreciably soluble, but suspensions of the salts as solids in solvents in which the salts are only slightly soluble are also a viable option. Alcohols, such as propanol, isopropanol, butanol, isobutanol, and t-butanol, and preferably methanol and ethanol are useful because the alkali metal salts are slightly soluble in them. In cases where the desired product is an alkoxysilane, it is preferable to use an alcohol corresponding to the silane alkoxy group to prevent transesterification at the silicon ester. Alternatively, nonprotic solvents can be used. Examples of appropriate solvents are ethers or polyethers such as glyme, diglyme, and dioxanes; N,N-dimethylformamide; N,N-dimethylacetamide; dimethylsulfoxide; N-methylpyrrolidinone; or hexamethylphosphommide. Once a solution, suspension, or combination thereof of the salt of the thioacid has been prepared, the second step is to react it with the appropriate haloalkylsilane. This may be accomplished by stirring a mixture of the haloalkylsilane with the solution, suspension, or combination thereof of the salt of the thioacid at temperatures corresponding to the liquid range of the solvent for a period of time sufficient to complete substantially the reaction. Preferable temperatures are those at which the salt is appreciably soluble in the solvent and at which the reaction proceeds at an acceptable rate without excessive side reactions. With reactions starting from chioroalkylsilanes in which the chlorine atom is not allylic or benzylic, preferable temperatures are in the range of 60° to 160° C. Reaction times can range from one or several hours to several days. For alcohol solvents where the alcohol contains four carbon atoms or fewer, the most preferred temperature is at or near reflux. When diglyme is used as a solvent, the most preferred temperature is in the range of 70° to 120° C., depending on the thioacid salt used. If the haloalkylsilane is a bromoalkylsilane or a chloroalkylsilane in which the chlorine atom is allylic or benzylic, temperature reductions of 30° to 60° C. are appropriate relative to those appropriate for non-benzylic or nonallylic chloroalkylsilanes because of the greater reactivity of the bromo group. Bromoalkylsilanes are preferred over chloroalkylsilanes because of their greater reactivity, lower temperatures required, and greater ease in filtration or centrifugation of the coproduct alkali metal halide. This preference, however, can be overridden by the lower cost of the chloroalkylsilanes, especially for those containing the halogen in the allylic or benzylic position. For reactions between straight chain chloroalkylethoxysilanes and sodium thiocarboxylates to form thiocarboxylate ester ethoxysilanes, it is preferable to use ethanol at reflux for 10 to 20 hours if 5 to 20 percent mercaptosilane is acceptable in the product. Otherwise, diglyme would be an excellent choice, in which the reaction would be run preferably in the range of 80° to 120° C. for one to three hours. Upon completion of the reaction the salts and solvent should be removed, and the product may be distilled to achieve higher purity.

If the salt of the thioacid to be used is not commercially available, its preparation may be accomplished by one of two methods, described below as Method A and Method B. Method A involves adding the alkali metal or a base derived from the alkali metal to the thioacid. The reaction occurs at ambient temperature. Appropriate bases include alkali metal alkoxides, hydrides, carbonates, and bicarbonates. Solvents, such as toluene, xylene, benzene, aliphatic hydrocarbons, ethers, and alcohols may be used to prepare the alkali metal derivatives. In Method B, acid chlorides or acid anhydrides would be converted directly to the salt of the thioacid by reaction with the alkali metal sulfide or hydrosulfide. Hydrated or partially hydrous alkali metal sulfides or hydrosulfides are available; however, anhydrous or nearly anhydrous alkali metal sulfides or hydrosulfides are preferred. Hydrous materials can be used, however, but with loss in yield and hydrogen sulfide formation as a coproduct. The reaction involves addition of the acid chloride or acid anhydride to the solution or suspension of the alkali metal sulfide and/or hydrosulfide and heating at temperatures ranging from ambient to the reflux temperature of the solvent for a period of time sufficient largely to complete the reaction, as evidenced by the formation of the coproduct salts.

If the alkali metal salt of the thioacid is prepared in such a way that an alcohol is present, either because it was used as a solvent, or because it formed, as for example, by the reaction of a thioacid with an alkali metal alkoxide, it may be desirable to remove the alcohol if a product low in mercaptosilane is desired. In this case, it would be necessary to remove the alcohol prior to reaction of the salt of the thioacid with the haloalkylsilane. This could be done by distillation or evaporation. Alcohols, such as methanol, ethanol, propanol, isopropanol, butanol, isobutanol, and t-butanol are preferably removed by azeotropic distillation with benzene, toluene, xylene, or aliphatic hydrocarbons. Toluene and xylene are preferred.

Utility

The blocked mercaptosilanes described herein are useful as coupling agents for organic polymers (i.e., rubbers) and inorganic fillers. The blocked mercaptosilanes are unique in that the high efficiency of the mercapto group can be utilized without the detrimental side effects typically associated with the use of mercaptosilanes, such as high processing viscosity, less than desirable filler dispersion, premature curing (scorch), and odor. These benefits are accomplished because the mercaptan group initially is nonreactive because of the blocking group. The blocking group substantially prevents the silane from coupling to the organic polymer during the compounding of the rubber. Generally, only the reaction of the silane —Si$X^1X^2X^3$ group with the filler can occur at this stage of the compounding process. Thus, substantial coupling of the filler to the polymer is precluded during mixing, thereby minimizing the undesirable premature curing (scorch) and the associated undesirable increase in viscosity. One can achieve better cured filled rubber properties, such as a balance of high modulus and abrasion resistance, because of the avoidance of premature curing.

The number of methylene groups between the silicon and G group, denoted by m, and sulfur (blocked mercaptan) and G group, denoted by n, improves coupling because the methylene group mitigates excessive steric interactions between the silane and the filler and polymer. Two successive methylene groups mitigate steric interactions even further and also add flexibility to the chemical structure of the silane, thereby enhancing its ability to accommodate the positional and orientational constraints imposed by the morphologies of the surfaces of both the rubber and filler at the interphase, at the molecular level. The silane flexibility becomes increasingly important as the total number of silicon and sulfur atoms bound to G increases from 3 to 4 and beyond. Tighter structures containing secondary and especially, tertiary carbon atoms; ring structures; and especially, aromatic structures on G near silicon and/or sulfur, are more rigid and cannot readily orient to meet available binding sites on silica and polymer. This would tend to leave sulfur groups unbound to polymer, thereby reducing the efficiency by which the principle of multiple bonding of silane to polymer via multiple blocked mercapto groups on silane, is realized.

The G group from which silicon and blocked mercapto group emanate through one or more methylene groups from a cyclic structure also improves coupling because the geometry of the cyclic structure naturally directs the emanating groups away from each other. This keeps them from getting in each other's way and also forces them to orient in divergent directions, so that silicon can bond to the filler, while sulfur bonds to the polymer phase. Aromatic cyclic structures for G are very rigid. Thus, although they direct silicon and blocked mercapto group in diverging directions, their rigidity limits freedom of orientation. The aliphatic cyclic G structures, because they do not contain the conjugated double bonds, are more flexible. They combine the advantages of divergent silicon and sulfur orientations from a cyclic structure and flexibility of the aliphatic cyclic structure.

One embodiment of the present invention is a rubber composition comprising:
 a) a blocked mercaptosilane of formula 1;
 b) an organic polymer;
 c) a filler; and optionally,
 d) other additives and curatives.

Another embodiment involves the use of these blocked mercaptosilanes of the present invention. One or more of the blocked mercaptosilanes are mixed with the organic polymer before, during, or after the compounding of the filler into the organic polymer. In a preferred embodiment the silanes are added before or during the compounding of the filler into the organic polymer, because these silanes facilitate and improve the dispersion of the filler. The total amount of silane present in the resulting combination should be about 0.05 to about 25 parts by weight per hundred parts by weight of organic polymer (phr), more preferably 1 to 10 phr. Fillers can be used in quantities ranging from about 5 to 100 phr, more preferably from 25 to 80 phr.

When reaction of the mixture to couple the filler to the polymer is desired, a deblocking agent is added to the mixture to deblock the blocked mercaptosilane. The deblocking agent may be added at quantities ranging from about 0.1 to about 5 phr, more preferably in the range of from 0.5 to 3 phr. If alcohol or water is present (as is common) in the mixture, a catalyst (e.g., tertiary amines, Lewis acids, or thiols) may be used to initiate and promote the loss of the blocking group by hydrolysis or alcoholysis to liberate the corresponding mercaptosilane. Alternatively, the deblocking agent may be a nucleophile containing a hydrogen atom sufficiently labile such that the hydrogen atom could be transferred to the site of the original blocking group to form the mercaptosilane. Thus, with a blocking group acceptor molecule, an exchange of hydrogen from the nucleophile would occur with the blocking group of the blocked mercaptosilane to form the mercaptosilane and the corresponding derivative of the nucleophile containing the original blocking group. This transfer of the blocking group from the silane to the nucleophile could be driven, for example, by a greater thermodynamic stability of the products (mercaptosilane and nucleophile containing the blocking group) relative to the initial reactants (blocked mercaptosilane and nucleophile). For example, if the nucleophile were an amine containing an N—H bond, transfer of the blocking group from the blocked mercaptosilane would yield the mercaptosilane and one of several classes of amides corresponding to the type of blocking group used. For example, carboxyl blocking groups deblocked by amines would yield amides, sulfonyl blocking groups deblocked by amines would yield sulfonamides, sulfinyl blocking groups deblocked by amines would yield sulfinamides, phosphonyl blocking groups deblocked by amines would yield phosphonamides, phosphinyl blocking groups deblocked by amines would yield phosphinamides. What is important is that regardless of the blocking group initially present on the blocked mercaptosilane and regardless of the deblocking agent used, the initially substantially inactive (from the standpoint of coupling to the organic polymer) blocked mercaptosilane is substantially converted at the desired point in the rubber compounding procedure to the active mercaptosilane. It is noted that partial amounts of the nucleophile may be used (i.e., a stoichiometric deficiency), if one were to deblock only part of the blocked mercaptosilane to control the degree of vulcanization of a specific formulation.

Water typically is present on the inorganic filler as a hydrate, or bound to a filler in the form of a hydroxyl group. The deblocking agent could be added in the curative package or, alternatively, at any other stage in the compounding process as a single component. Examples of nucleophiles would include any primary or secondary amines, or amines containing C=N double bonds, such as imines or guanidines, with the proviso that said amine contains at least one N—H (nitrogen-hydrogen) bond. Numerous specific examples of guanidines, amines, and imines well known in the art, which are useful as components in curatives for rubber, are cited in J. Van Alphen, *Rubber Chemicals*, (Plastics and Rubber Research Institute TNO, Delft, Holland, 1973). Some examples include N,N'-diphenylguanidine, N,N',N"-triphenylguanidine, N,N'-di-ortho-tolylguanidine, orthobiguanide, hexamethylenetetramine, cyclohexylethylamine, dibutylamine, and 4,4'-diaminodiphenylmethane. Any general acid catalysts used to transesterify esters, such as Bronsted or Lewis acids, could be used as catalysts.

The rubber composition need not be, but preferably is, essentially free of functionalized siloxanes, especially those of the type disclosed in Australian Patent AU-A-10082/97, which is incorporated herein by reference. Most preferably, the rubber composition is free of functionalized siloxanes.

In practice, sulfur vulcanized rubber products typically are prepared by thermomechanically mixing rubber and various ingredients in a sequentially stepwise manner followed by shaping and curing the compounded rubber to form a vulcanized product. First, for the aforesaid mixing of the rubber and various ingredients, typically exclusive of sulfur and sulfur vulcanization accelerators (collectively "curing agents"), the rubber(s) and various rubber compounding ingredients typically are blended in at least one, and often (in the case of silica filled low rolling resistance tires) two, preparatory thermomechanical mixing stage(s) in suitable mixers. Such preparatory mixing is referred to as nonproductive mixing or nonproductive mixing steps or stages. Such preparatory mixing usually is conducted at temperatures up to 140° to 200° C. and often up to 150° to 180° C. Subsequent to such preparatory mix stages, in a final mixing stage, sometimes referred to as a productive mix stage, deblocking agent (in the case of this invention), curing agents, and possibly one or more additional ingredients are mixed with the rubber compound or composition, typically at a temperature in a range of 50° to 130° C., which is a lower temperature than the temperatures utilized in the preparatory mix stages to prevent or retard premature curing of the sulfur curable rubber, which is sometimes referred to as scorching of the rubber composition. The rubber mixture, sometimes referred to as a rubber compound or composition, typically is allowed to cool, sometimes after or during a process intermediate mill mixing, between the aforesaid various mixing steps, for example, to a temperature of about 50° C. or lower. When it is desired to mold and to cure the rubber, the rubber is placed into the appropriate mold at about at least 130° C. and up to about 200° C., which will cause the vulcanization of the rubber by the mercapto groups on the mercaptosilane and any other free sulfur sources in the rubber mixture.

By thermomechanical mixing, it is meant that the rubber compound, or composition of rubber and rubber compounding ingredients, is mixed in a rubber mixture under high shear conditions where it autogenously heats up as a result of the mixing primarily due to shear and associated friction within the rubber mixture in the rubber mixer. Several chemical reactions may occur at various steps in the mixing and curing processes.

The first reaction is a relatively fast reaction and is considered herein to take place between the filler and the $SiX_3$ group of the blocked mercaptosilane. Such reaction may occur at a relatively low temperature such as, for example, at about 120° C. The second and third reactions are considered herein to be the deblocking of the mercaptosilane and the reaction which takes place between the sulfuric part of the organosilane (after deblocking), and the sulfur vulcanizable rubber at a higher temperature, for example, above about 140° C.

Another sulfur source may be used, for example, in the form of elemental sulfur as $S_g$. A sulfur donor is considered herein as a sulfur containing compound which liberates free, or elemental, sulfur at a temperature in a range of 140° to 190° C. Examples of such sulfur donors may be, but are not limited to, polysulfide vulcanization accelerators and organosilane polysulfides with at least two connecting sulfur atoms in its polysulfide bridge. The amount of free sulfur source addition to the mixture can be controlled or manipulated as a matter of choice relatively independently from the addition of the aforesaid blocked mercaptosilane. Thus, for example, the independent addition of a sulfur source may be manipulated by the amount of addition thereof and by sequence of addition relative to addition of other ingredients to the rubber mixture.

Addition of an alkyl silane to the coupling agent system (blocked mercaptosilane plus additional free sulfur source and/or vulcanization accelerator) typically in a mole ratio of alkyl silane to blocked mercaptosilane in a range of 1/50 to 1/2 promotes an even better control of rubber composition processing and aging.

In an embodiment of the present invention, a rubber composition is prepared by a process which comprises the sequential steps of:

(A) thermomechanically mixing, in at least one preparatory mixing step, to a temperature of 140° to 200° C., alternatively to 140° to 190° C., for a total mixing time of 2 to 20 minutes, alternatively 4 to 15 minutes, for such mixing step(s);
  (i) 100 parts by weight of at least one sulfur vulcanizable rubber selected from conjugated diene homopolymers and copolymers, and copolymers of at least one conjugated diene and aromatic vinyl compound,
  (ii) 5 to 100 phr (parts per hundred rubber), preferably 25 to 80 phr, of particulate filler, wherein preferably the filler contains 1 to 85 weight percent carbon black,
  (iii) 0.05 to 20 parts by weight filler of at least one blocked mercaptosilane;

(B) subsequently blending therewith, in a final thermomechanical mixing step at a temperature to 50° to 130° C. for a time sufficient to blend the rubber, preferably between 1 to 30 minutes, more preferably 1 to 3 minutes, at least one deblocking agent at about 0.05 to 20 parts by weight of the filler and a curing agent at 0 to 5 phr; and optionally (C) curing said mixture at a temperature of 130° to 200° C. for about 5 to 60 minutes.

In another embodiment of the present invention, the process may also comprise the additional steps of preparing an assembly of a tire or sulfur vulcanizable rubber with a tread comprised of the rubber composition prepared according to this invention and vulcanizing the assembly at a temperature in a range of 130° to 200° C.

Suitable organic polymers and fillers are well known in the art and are described in numerous texts, of which two examples include *The Vanderbilt Rubber Handbook*, R. F. Ohm, ed. (R. T. Vanderbilt Company, Inc., Norwalk, Conn., 1990), and *Manual for the Rubber Industry*, T. Kempermann, S. Koch, and J. Sumner, eds. (Bayer A G, Leverkusen, Germany, 1993). Representative examples of suitable polymers include solution styrene-butadiene rubber (sSBR), styrene-butadiene rubber (SBR), natural rubber (NR), polybutadiene (BR), ethylene-propylene co- and ter-polymers (EP, EPDM), and acrylonitrile-butadiene rubber (NBR). The rubber composition is comprised of at least one diene-based elastomer, or rubber. Suitable conjugated dienes are isoprene and 1,3-butadiene and suitable vinyl aromatic compounds are styrene and alpha methyl styrene. Thus, the rubber is a sulfur curable rubber. Such diene based elastomer, or rubber, may be selected, for example, from at least one of cis-1,4-polyisoprene rubber (natural and/or synthetic, and preferably natural rubber), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35 percent to 50 percent vinyl), high vinyl polybutadiene rubber (50 percent to 75 percent vinyl), styrene/isoprene copolymers, emulsion polymerization prepared styrene/butadiene/acrylonitrile terpolymer rubber and butadiene/acrylonitrile copolymer rubber. An emulsion polymerization derived styrene/butadiene (eSBR) might be used having a relatively conventional styrene content of 20 percent to 28 percent bound styrene or, for some applications, an eSBR having a medium to relatively high bound styrene content, namely, a bound styrene content of 30 percent to 45 percent. Emulsion polymerization prepared styrene/butadiene/acrylonitrile terpolymer rubbers containing 2 to 40 weight percent bound acrylonitrile in the terpolymer are also contemplated as diene based rubbers for use in this invention.

The solution polymerization prepared SBR (sSBR) typically has a bound styrene content in a range of 5 to 50 percent, preferably 9 to 36 percent. Polybutadiene elastomer may be conveniently characterized, for example, by having at least a 90 weight percent cis-1,4-content.

Representative examples of suitable filler materials include metal oxides, such as silica (pyrogenic and precipitated), titanium dioxide, aluminosilicate and alumina, siliceous materials including clays and talc, and carbon black. Particulate, precipitated silica is also sometimes used for such purpose, particularly when the silica is used in connection with a silane. In some cases, a combination of silica and carbon black is utilized for reinforcing fillers for various rubber products, including treads for tires. Alumina can be used either alone or in combination with silica. The term "alumina" can be described herein as aluminum oxide, or $Al_2O_3$. The fillers may be hydrated or in anhydrous form. Use of alumina in rubber compositions can be shown, for example, in U.S. Pat. No. 5,116,886 and EP 631,982.

In another embodiment of the present invention, the blocked mercaptosilane may be premixed, or prereacted, with the filler particles or added to the rubber mix during the rubber and filler processing, or mixing stage. If the silane and filler are added separately to the rubber mix during the rubber and filler mixing, or processing stage, it is considered that the blocked mercaptosilane then combines in situ with the filler.

The vulcanized rubber composition should contain a sufficient amount of filler to contribute a reasonably high modulus and high resistance to tear. The combined weight of the filler may be as low as about 5 to 100 phr, but is more preferably from 25 phr to 85 phr.

In another embodiment of the present invention, precipitated silicas are used as the filler. The silica may be characterized by having a BET surface area, as measured using nitrogen gas, preferably in the range of 40 to 600 $m^2/g$, and more usually in a range of 50 to 300 $m^2/g$. The silica typically may also be characterized by having a dibutylphthalate (DBP) absorption value in a range of 100 to 350, and more usually 150 to 300. Further, the silica, as well as the aforesaid alumina and aluminosilicate, may be expected to have a CTAB surface area in a range of 100 to 220. The CTAB surface area is the external surface area as evaluated by cetyl trimethylammonium bromide with a pH of 9. The method is described in ASTM D 3849.

Mercury porosity surface area is the specific surface area determined by mercury porosimetry. For such technique, mercury is penetrated into the pores of the sample after a thermal treatment to remove volatiles. Set up conditions may be suitably described as using a 100 mg sample, removing volatiles during two hours at 105° C. and ambient atmospheric pressure, ambient to 2000 bars pressure measuring range. Such evaluation may be performed according to the method described in Winslow, Shapiro in ASTM page 39 (1959) or according to DIN 66133. For such an evaluation, a CARLO-ERBA Porosimeter 2000 might be used. The average mercury porosity specific surface area for the silica should be in a range of 100 to 300 $m^2/g$.

A suitable pore size distribution for the silica, alumina, and aluminosilicate according to such mercury porosity evaluation is considered herein to be:

5 percent or less of its pores have a diameter of less than about 10 nm; 60 percent to 90 percent of its pores have a diameter of 10 to 100 nm; 10 percent to 30 percent of its pores have a diameter of 100 to 1,000 nm; and 5 percent to 20 percent of its pores have a diameter of greater than about 1,000 nm.

The silica might be expected to have an average ultimate particle size, for example, in the range of 0.01 to 0.05 µm as determined by the electron microscope, although the silica particles may be even smaller, or possibly larger, in size. Various commercially available silicas may be considered for use in this invention such as, from PPG Industries under the HI-SIL trademark with designations HI-SIL 210, 243, etc.; silicas available from Rhone-Poulenc, with, for example, designation of ZEOSIL 1165MP; silicas available from Degussa with, for example, designations VN2 and VN3, etc.; and silicas commercially available from Huber having, for example, a designation of HUBERSIL 8745.

In another embodiment of the present invention, where it is desired for the rubber composition, which contains both a siliceous filler such as silica, alumina and/or aluminosilicates and also carbon black reinforcing pigments, to be primarily reinforced with silica as the reinforcing pigment, it is often preferable that the weight ratio of such siliceous fillers to carbon black is at least 3/1 and preferably at least 10/1 and, thus, in a range of 3/1 to 30/1. The filler may be comprised of 15 to 95 weight percent precipitated silica, alumina, and/or aluminosilicate and, correspondingly 5 to 85 weight percent carbon black, wherein the carbon black has a CTAB value in a range of 80 to 150. Alternatively, the filler can be comprised of 60 to 95 weight percent of said silica, alumina, and/or aluminosilicate and, correspondingly, 40 to 5 weight percent carbon black. The siliceous filler and carbon black may be preblended or blended together in the manufacture of the vulcanized rubber.

The rubber composition may be compounded by methods known in the rubber compounding art, such as mixing the various sulfur-vulcanizable constituent rubbers with various commonly used additive materials. Examples of such commonly used additive materials include curing aids, such as sulfur, activators, retarders and accelerators, processing additives, such as oils, resins including tackifying resins, silicas, plasticizers, fillers, pigments, fatty acid, zinc oxide, waxes, antioxidants and antiozonants, peptizing agents, and reinforcing materials, such as, for example, carbon black. Depending on the intended use of the sulfur vulcanizable and sulfur vulcanized material (rubbers), the additives mentioned above are selected and commonly used in conventional amounts.

The vulcanization may be conducted in the presence of an additional sulfur vulcanizing agent. Examples of suitable sulfur vulcanizing agents include, for example, elemental sulfur (free sulfur) or sulfur donating vulcanizing agents, for example, an amino disulfide, polymeric polysulfide, or sulfur olefin adducts which are conventionally added in the final, productive, rubber composition mixing step. The sulfur vulcanizing agents (which are common in the art) are used, or added in the productive mixing stage, in an amount ranging from 0.4 to 3 phr, or even, in some circumstances, up to about 8 phr, with a range of from 1.5 to 2.5 phr, sometimes from 2 to 2.5 phr, being preferred.

Vulcanization accelerators, i.e., additional sulfur donors, may be used herein. It is appreciated that they may be, for example, of the type such as, for example, benzothiazole, alkyl thiuram disulfide, guanidine derivatives, and thiocarbamates. Representative of such accelerators are, for example, but are not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine) and dithiobis(dibenzyl amine). Other additional sulfur donors, may be, for example, thiuram and morpholine derivatives. Representative of such donors are, for example, but not limited to, dimorpholine disulfide, dimorpholine tetrasulfide, tetramethyl thiuram tetrasulfide, benzothiazyl-2,N-dithiomorpholide, thioplasts, dipentamethylenethiuram hexasulfide, and disulfidecaprolactam.

Accelerators are used to control the time and/or temperature required for vulcanization and to improve the properties of the vulcanizate. In one embodiment, a single accelerator system may be used, i.e., a primary accelerator. Conventionally and preferably, a primary accelerator(s) is used in total amounts ranging from 0.5 to 4 phr, preferably 0.8 to 1.5 phr. Combinations of a primary and a secondary accelerator might be used with the secondary accelerator being used in smaller amounts (of 0.05 to 3 phr) in order to activate and to improve the properties of the vulcanizate. Delayed action accelerators may be used. Vulcanization retarders might also be used. Suitable types of accelerators are amines, disulfides, guanidines, thioureas, thiazoles, thiurams, sulfonamides, dithiocarbamates, and xanthates. Preferably, the primary accelerator is a sulfenamide. If a second accelerator is used, the secondary accelerator is preferably a guanidine, dithiocarbamate, or thiuram compound.

Typical amounts of tackifier resins, if used, comprise 0.5 to 10 phr, usually 1 to 5 phr. Typical amounts of processing aids comprise 1 to 50 phr. Such processing aids include, for example, aromatic, naphthenic, and/or paraffinic processing oils. Typical amounts of antioxidants comprise 1 to 5 phr. Representative antioxidants may be, for example, diphenyl-p-phenylenediamine and others such as those disclosed in the *Vanderbilt Rubber Handbook* (1978), pages 344-46. Typical amounts of antiozonants comprise 1 to 5 phr. Typical amounts of fatty acids, which, if used, can include stearic acid, comprise 0.5 to 3 phr. Typical amounts of zinc oxide comprise 2 to 5 phr. Typical amounts of waxes comprise 1 to 5 phr. Often microcrystalline waxes are used. Typical amounts of peptizers comprise 0.1 to 1 phr. Typical peptizers may be, for example, pentachlorothiophenol and dibenzamidodiphenyl disulfide.

In still another embodiment of the present invention, the rubber composition of this invention can be used for various purposes. For example, it can be used for various tire compounds. Such tires can be built, shaped, molded, and cured by various methods which are known and will be readily apparent to those having skill in such art.

All references cited are incorporated herein as they are relevant to the present invention.

The invention may be better understood by reference to the following examples in which the parts and percentages are by weight unless otherwise indicated.

COMPARATIVE EXAMPLE A

Preparation of
3-(octanoylthio)-1-propyltriethoxysilane

Into a 12-liter, three-necked round bottom flask equipped with mechanical stirrer, addition funnel, thermocouple, heating mantle, N$_2$ inlet, and temperature controller were charged 3-mercaptopropyltriethoxysilane (1,021 grams, 3.73 moles purchase as SILQUEST® A-1891 silane from General Electric Company), triethylamine (433 grams), and hexane (3,000 ml). The solution was cooled in an ice bath, and octanoyl chloride (693 grams, 4.25 moles) were added over a two hour period via the addition funnel. After addition of the acid chloride was complete, the mixture was filtered two times, first through a 0.1 μm filter and then through a 0.01 μm filter, using a pressure filter, to remove the salt. The solvent was removed under vacuum. The remaining yellow liquid was vacuum distilled to yield 1,349 grams of octanoylthiopropyltriethoxysilane as a clear, very light yellow liquid. The yield was 87 percent.

EXAMPLE 1

Preparation of (2-triethoxysilylethyl)-bis-(3-thia-4-oxohexyl)cyclohexane

This example illustrates the preparation of a thiocarboxylate alkoxysilane from a silane containing two vinyl groups through the formation of an intermediate thioacetate silane.

The preparation of the (2-trimethoxysilylethyl)divinylcyclohexane was prepared by hydrosilation. Into a 5 L, three-neck round bottomed flask equipped with magnetic stir bar, temperature probe/controller, heating mantle, addition funnel, condenser, and air inlet were charged trivinylcyclohexane (2,001.1 grams, 12.3 moles) and VCAT catalysts (1.96 grams, 0.01534 gram platinium). Air was bubbled into the vinyl silane by means of the air inlet where the tube was below the surface of the silane. The reaction mixture was heated to 110° C. and the trimethoxysilane (1,204 grams, 9.9 moles) was added over a 3.5 hour period. The temperature of the reaction mixture increased to a maximum value of 130° C. The reaction mixture was cooled to room temperature and 1,3,5-trimethyl-2,4,6-tris(3,5-di-tert-butyl-4-hydroxylbenzyl)benzene (3 grams, 0.004 mole) was added. The reaction mixture was distilled at 122° C. and 1 mmHg pressure to give 1,427 grams of (2-trimethoxysilylethyl)divinylcyclohexane, The yield was 51 percent.

The (2-triethoxysilylethyl)divinylcyclohexane was prepared by transesterification. Into a 3 L, three-neck round bottomed flask equipped with magnetic stir bar, temperature probe/controller, heating mantle, addition funnel, distilling head and condenser, and nitrogen inlet were charged (2-trimethoxysilylethyl)divinylcyclohexane (284 grams, 2.33 moles), sodium ethoxide in ethanol (49 grams of 21% sodium ethoxide, purchased from Aldrich Chemical) and ethanol (777 grams, 16.9 moles). The reaction mixture was heated and the methanol and ethanol were removed by distillation at atmospheric pressure. The crude product was then distilled at 106° C. and under reduced pressure of 0.4 mmHg to give 675 grams of product, 89 percent yield.

The (2-triethoxysilylethyl)bis-(3-thia-4-oxopentyl)cyclohexane was prepared by addition of thioacetic acid to the divinylsilane. Into a 1 L, three-neck round bottomed flask equipped with magnetic stir bar, temperature probe/controller, heating mantle, addition funnel, condenser, air inlet and a sodium hydroxide scrubber, was charged thioacetic acid (210 grams, 2.71 moles). The (2-triethoxysilylethyl)divinylcyclohexane (400 grams, 1.23 moles) was added slowly over a period of 30 minutes and at room temperature by means of an addition funnel. The reaction was an exothermic reaction. The temperature of the mixture increased to 94.6° C. The mixture was stirred for 2.5 hours and allowed to cool to 38.8° C. Additional thioacetic acid (10 grams, 0.13 moles) was added and a slight exothermal reaction was observed. The reaction mixture was stirred overnight (18 hours) at about 25° C. Analysis indicated that the reaction mixture contained less than 2 percent thioacetic acid. Its overall purity was 91 percent. The reaction mixture was further purified by a distillation using a Kugel apparatus under reduced pressure.

The dimercaptosilane intermediate was prepared by removing the acetyl groups from (2-triethoxysilylethyl)bis-(3-thia-4-oxopentyl)cyclohexane. Into a 5 L, three-neck round bottomed flask equipped with magnetic stir bar, temperature probe/controller, heating mantle, addition funnel, distilling head and condenser, 10-plate Oldershaw column and nitorgen inlet were charged (2-triethoxysilylethyl)bis-(3-thia-4-oxopentyl)cyclohexane (2,000 grams, 4.1 moles), ethanol (546.8 grams, 11.8 moles) and sodium ethoxide in ethanol (108 grams of a 21% sodium ethoxide in ethanol). The pH of the reaction mixture was about 8. The reaction mixture was heated to 88° C. for 24 hours to remove the ethyl acetate and ethanol from the reaction mixture. Twice ethanol (1 liter) was added to the mixture and the pH of the reaction mixture was increase to about 10 by the addition of 21% sodium ethoxide in ethanol (21 grams) and heated an additional 6.5 hours. The reaction mixture was cooled and then pressure filtered. The reaction mixture was stripped at a temperature less than 95° C. and 1 mmHg pressure. The stripped product was filtered to give (2-triethoxysilylethyl)bis(2-mercaptoethyl)cyclohexane (1398 grams, 3.5 moles, 86% yield).

The (2-triethoxysilylethyl)-bis-(3-thia-4-oxohexyl)cyclohexane was prepared by the acetylation of the bismercaptosilane. Into a 5 L, three-neck round bottomed flask equipped with magnetic stir bar, temperature probe/controller, ice/water bath, addition funnel and condenser were charged (2-triethoxysilylethyl)bis(2-mercaptoethyl)cyclohexane (1010.6 grams, 2.56 moles), triethylamine (700 grams, 6.93 moles) and methylene chloride (1000 grams). Propionyl chloride (473.8 grams, 5.12 moles) was added to the stirred reaction mixture over a 1.5 hour period. The reaction mixture temperature increased to 50° C. Additional propionyl chloride (45.4 grams, 0.49 mole) was added. The reaction mixture was filtered and the salts were mixed with 500 mL of methylene chloride and washed with three times with distilled water and twice with saturated sodium chloride solution. The organic phase was dried over anhydrous magnesium sulfate and then stripped at 124° C. and reduced pressure to remove the volatile components. The stripped product (1196 grams, 2.36 moles) was analyzed by GC/MS, NMR and LC and the yield was 92 percent.

One isomer of (2-triethoxysilylethyl)-bis-(3-thia-4-oxohexyl)cyclohexane has the following structure:

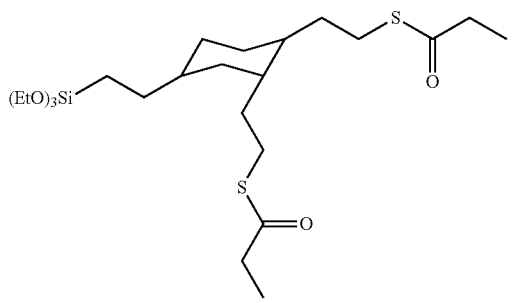

EXAMPLE 2 AND 3

The Use of Silanes in Low Rolling Resistant Tire Tread Formulation

A model low rolling resistance passenger tire tread formulation as described in Table 1 and a mix procedure were used to evaluate representative examples of the silanes of the present invention. The silane in Example 1 was mixed as follows in a "B" BANBURY (Farrell Corp.) mixer with a 103 cu. in. (1690 cc) chamber volume. The mixing of the rubber was done in two steps. The mixer was turned on with the mixer at 80 rpm and the cooling water at 71° C. The rubber polymers were added to the mixer and ram down mixed for 30 seconds. The silica and the other ingredients in Masterbatch 1 of Table 1 except for the silane and the oils were added to the mixer and ram down mixed for 60 seconds. The mixer speed was reduced to 35 rpm and then the silane and oils of the Materbatch 1 were added to the mixer and ram down for 60 seconds. The mixer throat was dusted down and the ingredients ram down mixed until the temperature reached 149° C. The ingredients were then mixed for an addition 3 minutes and 30 seconds, The mixer speed was adjusted to hold the temperature between 152 and 157° C. The rubber was dumped (removed from the mixer), a sheet was formed on a roll mill set at about 85° to 88° C., and then allowed to cool to ambient temperature.

In the second step, Masterbatch 1 was recharged into the mixer. The mixer's speed was 80 rpm, the cooling water was set at 71° C. and the batch pressure was set at 6 MPa. The Masterbatch 1 was ram down mixed for 30 seconds and then the temperature of the Masterbatch 1 was brought up to 149° C., and then the mixer's speed was reduce to 32 rpm. The zinc oxide and stearic acid were added (Masterbatch 2) and the rubber was mixed for 3 minutes and 20 seconds at temperatures between 152 and 157° C. During this mixing, the trimethylol propane was added (if needed). After mixing, the rubber was dumped (removed from the mixer), a sheet was formed on a roll mill set at about 85° to 88° C., and then allowed to cool to ambient temperature.

The rubber masterbatch and the curatives were mixed on a 15 cm×33 cm two roll mill that was heated to between 48° and 52° C. The sulfur and accelerators were added to the rubber (Masterbatches 1 &2) and thoroughly mixed on the roll mill and allowed to form a sheet. The sheet was cooled to ambient conditions for 24 hours before it was cured. The curing condition was 160° C. for 20 minutes.

Silane from Example 1 was compounded into the tire tread formulation according to the above procedure. The performance of the silanes prepared in Examples 1 was compared to the performance of silanes which are practiced in the prior art, bis-(3-triethoxysilyl-1-propyl)disulfide (TESPD), and Comparative Example A. The test procedures were described in the following ASTM methods:

| | |
|---|---|
| Mooney Scorch | ASTM D1646 |
| Mooney Viscosity | ASTM D1646 |
| Oscillating Disc Rheometer (ODR) | ASTM D2084 |
| Storage Modulus, Loss Modulus, Tensile and Elongation | ASTM D412 and D224 |
| DIN Abrasion | DIN Procedure 53516 |
| Heat Buildup | ASTM D623 |
| Percent Permanent Set | ASTM D623 |
| Shore A Hardness | ASTM D2240 |

The results of this procedure are tabulated below in Table 1.

TABLE 1

| Ingredients | Units | Example Number | | | |
| --- | --- | --- | --- | --- | --- |
| | | Comp. B | Comp. C | Example 2.00 | Example 3.00 |
| Masterbatch 1 | | | | | |
| SMR-10, natural rubber | phr | 10.00 | 10.00 | 10.00 | 10.00 |
| Budene 1207, polybutadiene | phr | 35.00 | 35.00 | 35.00 | 35.00 |
| Buna VSL 5025-1, oil-ext. sSBR | phr | 75.63 | 75.63 | 75.63 | 75.63 |
| N339, carbon black | phr | 12.00 | 12.00 | 12.00 | 12.00 |
| Ultrasil VN3 GR, silica | phr | 85.00 | 85.00 | 85.00 | 85.00 |
| Sundex 8125TN, process oil. | phr | 6.37 | 6.37 | 6.37 | 6.37 |
| Erucical H102, rapeseed oil | phr | 5.00 | 5.00 | 5.00 | 5.00 |
| Flexzone 7P, antiozonant | phr | 2.00 | 2.00 | 2.00 | 2.00 |
| TMQ | phr | 2.00 | 2.00 | 2.00 | 2.00 |
| Sunproof Improved, wax | phr | 2.50 | 2.50 | 2.50 | 2.50 |
| Kadox 720 C, zinc oxide | phr | — | — | — | — |
| Industrene R, stearic acid | phr | — | — | — | — |
| Aktiplast ST, disperser | phr | 4.00 | 4.00 | 4.00 | 4.00 |
| Silane TESPD | phr | 4.50 | — | — | — |
| Silane Comparative Example 1 | phr | — | 6.90 | — | — |
| Silane Example 2 | phr | — | — | 9.68 | 9.68 |
| TMP | phr | 2.50 | 2.50 | 2.50 | — |
| Masterbatch 2 | | | | | |
| Kadox 720 C, zinc oxide | phr | 2.50 | 2.50 | 2.50 | 2.50 |
| Industrene R, stearic acid | phr | 1.00 | 1.00 | 1.00 | 1.00 |
| TMP | phr | — | — | — | 2.50 |
| Catalysts | | | | | |
| Naugex MBT | | 0.10 | 0.10 | 0.10 | 0.10 |
| Diphenyl guanidine | | 2.00 | 2.00 | 2.00 | 2.00 |
| Delac S, CBS | | 2.00 | 2.00 | 2.00 | 2.00 |
| Rubbermakers sulfur 167 | | 2.20 | 2.20 | 2.20 | 2.20 |
| total | phr | 256.30 | 258.69 | 261.47 | 261.47 |
| Specific Gravity | g/cm3 | 1.21 | 1.21 | 1.22 | 1.21 |
| Physical Properties | | | | | |
| Mooney Viscosity at 100 Celsius ML1 + 3 | mooney units | 69.60 | 55.80 | 55.90 | 52.70 |
| Minimum Torque (Mooney Low) | dNm | 2.67 | 1.74 | 1.83 | 1.79 |
| Maximum Torque (Mooney High) | dNm | 19.31 | 18.17 | 19.89 | 19.40 |
| Torque (Max − Min) | dNm | 16.64 | 16.43 | 18.06 | 17.61 |
| 1.13 DNM RISE | min | 1.30 | 1.50 | 1.15 | 0.98 |
| 2.26 DNM RISE | min | 1.77 | 1.78 | 1.40 | 1.18 |
| Cure, 160 Celsius for 20 minutes | | | | | |
| T-10 | min | 1.65 | 1.70 | 1.37 | 1.15 |
| T-40 | min | 2.50 | 2.27 | 2.01 | 1.65 |
| T-95 | min | 13.36 | 15.00 | 19.80 | 17.62 |
| cure time | min | 20.00 | 20.00 | 20.00 | 20.00 |
| 50% Modulus | MPa | 1.40 | 1.57 | 1.57 | 1.50 |
| 100% Modulus | MPa | 2.53 | 2.83 | 2.80 | 2.80 |
| 300% Modulus | MPa | 12.20 | 11.87 | 12.23 | 12.80 |
| Reinforcement Index | | 4.82 | 4.19 | 4.37 | 4.57 |
| Tensile | MPa | 16.80 | 15.30 | 15.93 | 17.13 |
| Elongation | % | 425.20 | 406.40 | 410.40 | 416.90 |
| M300 − M100 | | 9.67 | 9.04 | 9.43 | 10.00 |
| Durometer Shore "A" | shore A | 66.80 | 67.90 | 68.90 | 68.50 |
| Zwick Rebound, Room Temperature | percent | 30.50 | 33.60 | 30.10 | 30.90 |
| Zwick Rebound, 70 Celsius | percent | 47.70 | 49.70 | 49.90 | 49.60 |
| Delta Rebound, 70 C. - RT | percent | 17.20 | 16.10 | 19.80 | 18.70 |

The data from Table 1 show an improvement in the delta rebound, an indicator of improve traction, and torque, an indicator of improved wear, while maintaining the other processing and physical properties when trimethylol propane was added as an activator.

EXAMPLES 4 AND 5

The rubber compounds described in Table 2 were prepared according to the procedures of Examples 2 and 3. The data from Table 2 show and improve in the delta rebound over the two comparative Example D and E.

TABLE 2

| Ingredients | Units | Comp. D | Comp. E | Example 4.00 | Example 5.00 |
|---|---|---|---|---|---|
| Masterbatch 1 | | | | | |
| SMR-10, natural rubber | phr | 10.00 | 10.00 | 10.00 | 10.00 |
| Budene 1207, polybutadiene | phr | 35.00 | 35.00 | 35.00 | 35.00 |
| Buna VSL 5025-1, oil-extended sSBR | phr | 75.63 | 75.63 | 75.63 | 75.63 |
| N 339, carbon black | phr | 12.00 | 12.00 | 12.00 | 12.00 |
| Ultrasil VN 3 GR, Silica | phr | 85.00 | 85.00 | 85.00 | 85.00 |
| Sundex 8125TN, process oil | phr | 6.37 | 6.37 | 6.37 | 6.37 |
| Erucical H 102, rapeseed oil | phr | 5.00 | 5.00 | 5.00 | 5.00 |
| Flexzone 7P, antiozonant | phr | 2.00 | 2.00 | 2.00 | 2.00 |
| TMQ | phr | 2.00 | 2.00 | 2.00 | 2.00 |
| Sunproof Improved, wax | phr | 2.50 | 2.50 | 2.50 | 2.50 |
| Kadox 720 C, zinc oxide | phr | — | — | 2.50 | — |
| Industrene R, stearic acid | phr | — | — | 1.00 | — |
| Aktiplast ST, disperser | phr | 4.00 | 4.00 | 4.00 | 4.00 |
| Silane TESPD | phr | 4.50 | — | — | — |
| Silane Comparative Example 1 | phr | — | 6.90 | — | — |
| Silane Example 2 | phr | — | — | 9.68 | 9.68 |
| TMP | phr | — | — | — | — |
| Masterbatch 2 | | | | | |
| Kadox 720 C, zinc oxide | phr | 2.50 | 2.50 | — | 2.50 |
| Industrene R, stearic acid | phr | 1.00 | 1.00 | — | 1.00 |
| TMP | phr | — | — | — | — |
| Catalysts | | | | | |
| Naugex MBT | phr | 0.10 | 0.10 | 0.10 | 0.10 |
| Diphenyl guanidine | phr | 2.00 | 2.00 | 2.00 | 2.00 |
| Delac S, CBS | phr | 2.00 | 2.00 | 2.00 | 2.00 |
| Rubbermakers sulfur 167 | phr | 2.20 | 2.20 | 2.20 | 2.20 |
| total | phr | 253.80 | 256.20 | 258.97 | 258.97 |
| Specific Gravity | g/cm³ | 1.21 | 1.21 | 1.21 | 1.21 |
| Physical Properties | | | | | |
| Mooney Viscosity at 100° Celsius ML 1 + 3 | Mooney units | 75.50 | 67.10 | 61.20 | 60.60 |
| Minimum Torque (Mooney Low) | dNm | 2.99 | 2.26 | 1.96 | 2.04 |
| Maximum Torque (Mooney High) | dNm | 18.52 | 17.40 | 17.55 | 17.82 |
| Torque (Max − Min) | dNm | 15.53 | 15.14 | 15.59 | 15.78 |
| 1.13 DNM RISE | minutes | 0.80 | 1.97 | 1.39 | 1.80 |
| 2.26 DNM RISE | minutes | 1.73 | 2.41 | 1.76 | 2.17 |
| Cure, 160° Celsius for 20 minutes | | | | | |
| T-10 | minutes | 1.41 | 2.24 | 1.64 | 2.05 |
| T-40 | minutes | 3.09 | 3.12 | 2.37 | 2.81 |
| T-95 | minutes | 11.20 | 10.87 | 12.23 | 12.22 |
| cure time | minutes | 20.00 | 20.00 | 20.00 | 20.00 |
| 50% Modulus | MPa | 1.20 | 1.33 | 1.20 | 1.20 |
| 100% Modulus | MPa | 2.00 | 2.40 | 2.10 | 2.17 |
| 300% Modulus | MPa | 10.47 | 11.03 | 10.53 | 10.53 |
| Reinforcement Index | | 5.24 | 4.60 | 5.01 | 4.86 |
| Tensile | MPa | 17.33 | 16.27 | 17.23 | 16.57 |
| Elongation | % | 470.40 | 446.60 | 474.00 | 462.80 |
| M300 − M100 | | 8.47 | 8.63 | 8.43 | 8.36 |
| Durometer Shore "A" | shore A | 62.60 | 64.40 | 63.00 | 64.60 |
| Zwick Rebound, Room Temperature | percent | 32.00 | 35.00 | 33.20 | 31.60 |
| Zwick Rebound, 70° Celsius | percent | 47.70 | 50.40 | 50.00 | 48.60 |
| Delta Rebound, 70° C. − RT | percent | 15.70 | 15.40 | 16.80 | 17.00 |

EXAMPLE 6

Preparation of (2-triethoxysilylethyl-bis-(3-thia-4-oxoundecyl)cyclohexane

This example illustrates the preparation of a thiocarboxylate alkoxysilane from a silane containing two vinyl groups and a thioacid. Into a 3 L, three-neck round bottomed flask equipped with magnetic stir bar, temperature probe/controller, heating mantle, addition funnel, condenser, air inlet and a sodium hydroxide scrubber, was charged thiooctanoic acid (780.1 grams, 4.87 moles). Air was bubbled into the thioacid by means of the air inlet where the tube was below the surface of the thioacid. (2-Triethoxysilylethyl)-divinylcyclohexane (755.0 grams, 2.31 moles) was added slowly to the thioacid by means of an addition funnel over a period of 32 minutes. The addition started at 22.3° C. and a slight exothermal reaction occurred which raised the temperature to 34.9° C. The reaction mixture was then slowly heated to 84.8° C. over 3 hours. Di-tert-butyl peroxide (1.1 grams) was added and stirred for 2 hours. 2,2'-Azoisobutyronitrile (1.2 grams, from Aldrich Chemical) was added and the mixture was heated for an additional 4.4 hours at 85° C. The thiooctanoic acid (32.4 grams) was removed under reduced pressure (0.5 mmHg) and elevated temperature of 167° C. to give 1,472.1 grams of product. $^{13}$C NMR analysis indicated that 95% reaction occurred between the thiooctanoic acid and the vinyl groups of (2-triethoxysilylethyl)divinylcyclohexane.

EXAMPLE 7

Preparation of (2-triethoxysilylethyl-bis(3-thia-4-oxohexyl)cyclohexane

This example illustrates the preparation of a thiocarboxylate alkoxysilane from a silane containing two vinyl groups and a thioacid. Into a 3 L, three-neck round bottomed flask equipped with magnetic stir bar, temperature probe/controller, heating mantle, addition funnel, condenser, air inlet and a sodium hydroxide scrubber, was charged thiopropanoic acid (591.8 grains, 6.49 moles). Air was bubbled into the thioacid by means of the air inlet where the tube was below the surface of the thioacid. (2-Triethoxysilylethyl)-divinylcyclohexane (1052.0 grams, 3.22 moles) was added to the thioacid by means of an addition funnel over a period of 15 minutes. The addition started at 21.0° C. and an exothermic reaction occurred which raised the temperature to 86.7° C. After 70 minutes, the reaction mixture was then heated to maintain a temperature of about 86° C. for an additional 20 minutes. 2,2'-Azoisobutyronitrile (1.2 grams, from Aldrich Chemical) was added and the mixture was heated for one hour at 86° C. Di-tert-butyl peroxide (2.0 grams) was charge to the reaction mixture and heated for 7 hours at 86° C. The thiopropanoic acid was removed under reduced pressure (0.5 mmHg) and elevated temperature of 70° C. to give the product.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A compound having the structure (2-triethoxysilylethyl) bis-(3-thia-4-oxopentyl)cyclohexane.

2. A method for making the compound of claim 1 comprising reacting a thioacetic acid with (2-triethoxysilylethyl)divinylcyclohexane.

3. The method of claim 1, wherein the reaction is catalyzed by UV radiation.

4. The method of claim 2, wherein the reaction is conducted in the presence of a free radical initiator.

5. The method of claim 4, wherein the free radical initiator is selected from the group consisting of air, peracid, ester of peracid, peroxide, hydroperoxide, peroxy-acetal, peroxy-ketal, azobisisobutyronitrile, 1,1-azobis(cyclohexanecarbonitrile) and azo-tert-butane.

6. The method of claim 4, wherein the reaction is conducted at a temperature below 90° C.

7. A rubber composition including a compound of claim 1.

8. A rubber composition comprising:
(a) a compound of claim 1;
(b) an organic polymer;
(c) a filler; and optionally,
(d) other additives and curatives.

9. The rubber composition of claim 8 wherein the organic polymer (b) is selected from the group consisting of solution styrene-butadiene rubber, emulsion styrene-butadiene rubber, natural rubber, polybutadiene rubber, ethylene-propylene copolymer, ethylene-propylene-diene monomer (EPDM), acrylonitrile-butadiene rubber, cis-1,4-polyisoprene rubber, 3,4-polyisoprene rubber, cis-1,4-polybutadiene rubber, medium vinyl polybutadiene rubber, high vinyl polybutadiene rubber, and mixtures thereof.

10. The rubber composition of claim 8 wherein the filler (c) is selected from the group consisting of pyrogenic silica, precipitated silica, titanium dioxide, aluminosilicate, alumina, clay, talc and carbon black.

11. A process for preparing a cured rubber composition comprising:
(A) thermomechanically mixing, in at least one preparatory mixing step, to a temperature of from 140° to 200° C. and for a total mixing time of 2 to 20 minutes,
(i) 100 parts by weight of at least one sulfur vulcanizable rubber selected from conjugated diene homopolymer, conjugated diene copolymer, and copolymer of at least one conjugated diene and aromatic vinyl compound,
(ii) 5 to 100 parts per hundred rubber of at least one particulate filler,
(iii) 0.05 to 20 parts by weight filler of a compound having the structure of claim 1;
(B) subsequently blending therewith, in a final thermomechanical mixing step at a temperature to 50° to 130° C., the rubber of step (A), at least one deblocking agent in an amount of from 0.05 to 20 parts by weight of the filler and a curing agent in an amount of from 0 to 5 parts per hundred parts rubber; and
(C) curing said mixture.

12. The process of claim 11, wherein the particulate filler is selected from the group consisting of pyrogenic silica, precipitated silica, titanium dioxide, aluminosilicate, alumina, clay, talc and carbon black.

13. The process of claim 11 wherein the sulfur vulcanizable rubber is selected from the group consisting of solution styrene-butadiene rubber, emulsion styrene-butadiene rubber, natural rubber, polybutadiene rubber, ethylene-propylene copolymer, ethylene-propylene-diene monomer (EPDM), acrylonitrile-butadiene rubber, cis-1,4-polyisoprene rubber, 3,4-polyisoprene rubber, cis-1,4-polybutadiene rubber, medium vinyl polybutadiene rubber and high vinyl polybutadiene rubber.

14. A free flowing filler composition comprising the compound of claim 1 and at least one particulate filler.

15. The free flowing filler composition of claim 14 wherein the particulate filler is selected from the group consisting of pyrogenic silica, precipitated silica, titanium dioxide, aluminosilicate, alumina, clay, talc and carbon black.

* * * * *